(12) United States Patent
Schwartz et al.

(10) Patent No.: US 7,838,490 B2
(45) Date of Patent: Nov. 23, 2010

(54) METHODS AND COMPOSITIONS FOR INHIBITION OF VASCULAR PERMEABILITY

(75) Inventors: Martin A. Schwartz, Earlysville, VA (US); Rebecca A. Stockton, Del Mar, CA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 365 days.

(21) Appl. No.: 11/997,957

(22) PCT Filed: Aug. 9, 2006

(86) PCT No.: PCT/US2006/031229

§ 371 (c)(1),
(2), (4) Date: Feb. 5, 2008

(87) PCT Pub. No.: WO2007/019563

PCT Pub. Date: Feb. 15, 2007

(65) Prior Publication Data

US 2009/0220487 A1    Sep. 3, 2009

Related U.S. Application Data

(60) Provisional application No. 60/706,597, filed on Aug. 9, 2005.

(51) Int. Cl.
*A61K 38/00* (2006.01)
(52) U.S. Cl. .......................................................... 514/2
(58) Field of Classification Search ........................ None
See application file for complete search history.

(56) References Cited

PUBLICATIONS

Feng et al. ("Regulation of the Cool/Pix proteins: key binding partners of the Cdc42/Rac targets, the p21-activated kinases." J. Biol. Chem., 2002, 277, 5644-50).*
Manser et al. ("PAK kinases are directly coupled to the PIX family of nucleotide exchange factors," Mol. Cell., 1998, 1, 183-92).*

"European Application No. 06801159.2 , Office Action mailed on Dec. 16, 2009", 1 pg.
"New Zealand Application Serial No. 566134 , First Examination Report Mailed, Feb. 26, 2010", 3 pgs.
"*Pharmaceutical Management Agency LTD* v *Commissioner of Patents*", R.P.C., 116, High Court of New Zealand—Wellington Registry, (1999), 752-774.
"Abstracts PS 0035-0363", *Intensive Care Medicine*, 32(1), (2006), 14-96.
"European Applicaion Serial No. 06801159.2, Search Report mailed on Sep. 18, 2009", 12 pgs.
"International Application Serial No. PCT/US06/31229, International Search Report mailed Aug. 17, 2007", 4 pgs.
"International Application Serial No. PCT/US06/31229, Written Opinion mailed Aug. 17, 2007", 4 pgs.
Garcia, J. G. N., et al., "Sphingosine 1—phosphate promotes endothelial cell barrier integrity by Edg-dependent cytoskeletal rearrangement", *Journal of Clinical Investigation*, 108(5);, (2001), 689-701.
Kiosses, W. B., et al., "A Dominant-Negative p65 PAK Peptide Inhibits Angiogenesis", *Circulation Research*, 90(6), (2002), 697-702.
Stockton, R. A., et al., "p21-activated kinase regulates endothelial permeability through modulation of contractility", *Journal of Biological Chemistry*, 279(45), (2004), 46621-46630.
Strohm, C., et al., "Inhibition of the ER-Kinase Cascade by PD98059 and U0126 Counteracts Ischemic Preconditioning in Pig Myocardium", *Journal of Cardiovascular Pharmacology™*, 369(2), (2000), 218-229.
Vouret-Craviari, V., et al., "Modulation of Rho GTPase activity in endothelial cells by selective proteinase-activated receptor (PAR)agonists", *Journal of Thrombosis and Haemostatis*, 1(5), (2003), 1103-1111.
Woolfolk, E., et al., "Intracellular Mechanisms Involved in Regulation of p-21 Activated Kinase by Angiotensin II in Vascular Smooth Muscle Cells", *Faseb Journal*, 19( 4, Suppl. S, Part 1), (Abstract 376.6), (Mar. 2005), p. A663.

* cited by examiner

*Primary Examiner*—Christina Bradley
(74) *Attorney, Agent, or Firm*—Schwegman, Lundberg & Woessner, P.A.

(57) ABSTRACT

The present invention relates to methods and compositions for regulating vascular permeability. The present invention relates to methods and compositions for blocking proteins and signal transduction pathways involved in increasing vascular permeability.

13 Claims, 14 Drawing Sheets

PIX binding peptide: YGRKKRRQRRRGPPPVIAPRPEHTKSVYTR-K+BIOTIN
　　　　　　　　　　　permeabilization　　　　PIX binding
　　　　　　　　　　　　　sequence　　　　　　　sequence Control Peptide: YGRKKRRQRRRGPPPVIAPAAEHAKSVVYTR-K+BIOTIN

METHODS AND COMPOSITIONS FOR INHIBITION OF VASCULAR PERMEABILITY

CROSS REFERENCE TO RELATED APPLICATIONS

This application is a national stage filing of International Application No. PCT/US2006/031229, filed on Aug. 9, 2006, which is entitled to priority pursuant to 35 U.S.C. §119(e) to U.S. provisional patent application No. 60/706,597, filed on Aug. 9, 2005, the entire disclosures of which are incorporated by reference herein.

STATEMENT REGARDING FEDERALLY SPONSORED RESEARCH OR DEVELOPMENT

This invention was made with United States Government support under Grant Nos. RO1 GM47214 and T32 HL07284, awarded by the National Institutes of Health. The United States Government has certain rights in the invention.

BACKGROUND

Passage of fluid and cells out of blood vessels is a significant contributing factor to inflammation, tissue injury, and death in a variety of circumstances. These include ischemic injury, toxic shock, allergic and immune reactions. Vascular permeability is regulated in part by cell-cell adhesions between endothelial cells.

The endothelial cell monolayer lining the vasculature forms a barrier that maintains the integrity of the blood fluid compartment, but permits passage of soluble factors and leukocytes in a regulated manner. Dysregulation of this process produces vascular leakage into underlying tissues, which accompanies the inflammation associated with pathological conditions involving edema. Edema associated with vascular permeability also occurs in ischemic injury due to the secretion of vascular endothelial growth factor (VEGF) by hypoxic tissues, which increases tissue damage in animal models of stroke and myocardial infarction. Vascular permeability is characterized by altered cell-cell contacts and the appearance of paracellular pores between adjacent cells. Integrity of the endothelial barrier is regulated in part by opposing roles of the actin cytoskeleton in which cortical F-actin stabilizes cell-cell contacts, whereas intracellular stress fibers exert tension to induce permeability.

Vascular permeability is a precisely regulated function that can contribute positively to immune responses and wound healing; however, leakage of fluid and immune cells into tissues can have serious and life-threatening consequences in a variety of diseases. Fluid accumulation in the lungs because of increased permeability of the pulmonary vasculature leading to respiratory insufficiency is a key element in acute respiratory distress syndrome. Vascular leak after stroke or myocardial infarction due to the release of VEGF by hypoxic tissues substantially increases tissue injury after these events. Vascular leak and tissue edema contribute to organ failure in sepsis.

Lung injury is a serious, often fatal, medical problem (Orfanos et al., 2004; Lionetti et al., 2005). It is usually caused by infection and can be exacerbated by mechanical ventilation to trigger leakage of fluid into the lungs, leading to respiratory insufficiency. Incidence of death in acute lung injury is in the range of 30-40% and no specific treatment is currently available.

The small GTPase Rac regulates formation and function of cell-cell adhesions in a number of systems. In epithelial and endothelial cell types, Rac is important for both the assembly of adherens and tight junctions and for their disruption during cell scattering or in response to agonists that trigger permeability. These complex effects suggest that different Rac effector pathways may differentially regulate cell-cell junctions. Precise temporal and spatial regulation of Rac and its effector pathways are likely to be critical for determining the balance between strengthening and disrupting cell-cell adhesions. However, the downstream pathways that govern these effects are poorly understood.

The p21-activated kinases (PAKs) are serine/threonine kinases activated downstream of Rac and Cdc42 that participate in multiple cellular functions, including motility, morphogenesis, and angiogenesis. GTP-bound Rac and Cdc42 bind to inactive PAK, releasing steric constraints imposed by a PAK autoinhibitory domain and permitting PAK auto-phosphorylation and activation. Numerous autophosphorylation sites have been identified that serve as markers for activated PAK. Prominent PAK downstream targets include LIM kinase, which regulates actin polymerization through its effect on cofilin, and myosin light chain (MLC). PAK2 catalyzes monophosphorylation of MLC at $Ser^{19}$ to increase contractility and trigger cell retraction. However, PAK can also inhibit MLC kinase and thereby limit MLC phosphorylation and retraction. Serine 141 on PAK2 is a site within the AID sequence that is phosphorylated during activation of the kinase. Phosphorylation of this site contributes to activation by blocking interaction of the AID with the kinase domain to relieve autoinhibition. In endothelial cells, expression of catalytically active PAK1 increased MLC phosphorylation and cell contractility, whereas inhibiting PAK reduced cell contractility. Thus, in these cells, the dominant effect of PAK appears to be the promotion of contractility.

It was previously demonstrated that activation of PAK in endothelial cell-cell junctions regulates vascular permeability in response to cytokines (Stockton, J. Biol. Chem. 279: 46621-46630). It did so by controlling phosphorylation of myosin light chain, which promotes cell retraction. PAK is known to regulate ERK1/2 activation (Frost, 1997, EMBO J. 16:6426-6438). Erk is also known to regulate vascular permeability (Verin, Am J Physiol Lung Cell Mol Physiol. 2000 279:L360-70; Borbiev Am J Physiol Lung Cell Mol Physiol. 2003 285:L43-54).

PAK can bind to a protein called PIX (alpha or beta isoforms), which in turn binds to another protein called GIT (isoforms 1 or 2) (reviewed in Turner, Curr Opin Cell Biol., 2001, 13:593-599.) GIT has been proposed to be a scaffold protein that enhances activation of Erk MAP kinase (Yin 2004, Mol. Cell Biol. 24:875-885). The PAK pathway seems to be involved in many events that stimulate vascular leak. GIT proteins are GTPase-activating proteins for ADP-ribosylation factor (ARF) small GTP-binding proteins.

The sequence within PAK which binds to PIXα and PIXβ is PPPVIAPRPEHTKSVYTR (SEQ ID NO:1) (Manser et al., Mol. Cell. 1998 1:2:183-92). The core sequence within PIX that binds GIT1/2 is: AALEEDAQILKVI (SEQ ID NO:2), corresponding to amino acid residues 685-698 for PIXα and amino acid residues 527-542 for PIXβ (Feng et al., 2002, J. Biol. Chem. 277:5644-5650). The core sequences within GIT1 and GIT2 that bind PIX proteins are the Spa2 homology domains (255-375 in GIT1) and the coiled coil regions (428-485 in GIT1) (Premont et al., 2004, Cell Signal 16:1001-1011). The region with GIT1 that binds MEK is also within the Spa homology domain (amino acid residues 255-375) (Haendeler et al., 2003, J. Biol. Chem. 278:50:49936-44).

PAK kinase is activated by the small GTPases Rac and Cdc42. It is sometimes found in a complex with two other proteins, namely PIX (α or β) and GIT (1 or 2). Pak binds directly to the PIX SH3 domain through an unconventional proline rich sequence in PAK. PIX then associates with GIT proteins through the extreme C-terminus of PIX and two regions within GIT: the Spa2 homology domains (amino acid residues 270-363) and the coiled coil (amino acid residues 428-485). GIT1 has also been found to be a scaffold protein for activation of Erk. GIT1 binds MEK1/2, the upstream kinases for Erk activation.

It was previously shown by Applicants that PAK kinase is critical for induction of vascular permeability by growth factors, inflammatory cytokines, and thrombin. PAK controlled permeability by regulation phosphorylation of myosin light chain kinase and increased cell contraction, which disrupts the cell-cell junctions that serve as a permeability barrier.

There is a long felt need in the art for compositions and methods to regulate vascular permeability. The present invention satisfies these needs.

SUMMARY OF THE INVENTION

A complex of proteins including PAK, PIX, GIT1 and GIT2, and MEK is essential for triggering permeability of endothelial monolayers in response to many cytokines, growth factors or mechanical stimulation. Vascular permeability is a major contributing factor to many pathological conditions that involve tissue injury and inflammation including acute lung injury, stroke, myocardial infarction, and infection. PAK could conceivably activate MLCK phosphorylation through several mechanisms. Potential pathways include direct phosphorylation of myosin (Chew et al., 1998) or caldesmon (Foster et al., 2000). Alternatively, this effect could involve phosphorylation of Raf or MEK1/2 to activate Erk (Frost et al., 1997; King et al., 1998), which can activate MLCK (Klemke et al., 1997). The present invention encompasses mechanisms by which PAK activates MLCK phosphorylation to induce vascular leak as well as compositions and methods to regulate this pathway.

The present invention is directed to compositions and methods for regulating vascular permeability, particularly inhibiting vascular permeability. More particularly, the present invention is directed to a method of regulating vascular permeability by blocking interactions of proteins important for triggering vascular permeability. The present invention provides peptides, and modifications, fragments, derivatives, homologs, and analogs thereof, which compete for interaction sites to disrupt the PAK-PIX-GIT-MEK complex or displace the complex from cell-cell junctions. Such peptides are referred to as competitive peptides or sequences herein. The peptides of the invention compete with, or regulate, at least one of PAK, PIX, GIT, and MEK. Therefore, the present invention encompasses regulating vascular permeability via related signal transduction pathways, comprising the use of regulators of at least one protein regulatory pathway selected from the group consisting of PAK, PIX, GIT, MEK, Erk, and MLCK, thereby regulating vascular permeability In one aspect, a peptide of the invention blocks binding of PAK to PIXα. In another aspect, a peptide of the invention blocks binding of PAK to PIXβ. In one aspect, a peptide of the invention blocks binding of PIX to GIT1. In another aspect, a peptide of the invention blocks binding of PIX to GIT2. In one aspect, a peptide of the invention blocks binding of MEK with GIT1. In one aspect, MEK is MEK1 or MEK2. In one aspect, peptides of the invention block Erk activation. In another aspect, peptides of the invention block Erk MAP kinase. In one aspect, peptides of the invention block signaling from PAK to Erk and then to MLCK. The invention further encompasses methods and compositions and to regulate Erk and MLCK downstream from PAK.

In one embodiment of the invention, peptides of the invention block protein complex formation or interaction. In one aspect, peptides of the invention block localization of protein complexes to cell-cell junctions.

In one aspect, vascular permeability is blocked by peptides of the invention in a subject in need thereof.

The following peptides are used herein:

```
SEQ ID NO: 1-PPPVIAPRPEHTKSVYTR

SEQ ID NO: 2-AALEEDAQILKVI

SEQ ID NO: 3-YGRKKRRQRRRG

SEQ ID NO: 4-YGRKKRRQRRRGPPPVIAPRPEHTKSVYTR

SEQ ID NO: 5-YGRKKRRQRRRGPPPVIAPAAEHAKSVVYTR

SEQ ID NO: 6-YGRKKRRQRRRGKPPAPPMRNTSTM

SEQ ID NO: 7-KPPAPPMRNTSTM
```

The following nucleic acids are used herein:

```
SEQ ID NO: 8-GGCCAAAGCUGCUAAGAAGUU

SEQ ID NO: 9-GGACGACGCCAUCUAUUCAUU

SEQ ID NO: 10-GCACACCCAUUGACUAUGCUU

SEQ ID NO: 11-GGACGCCACAUCUCCAUUGUU
```

Briefly, the function and/or origin of sequences used herein is:

SEQ ID NO:1 is a sequence within PAK which binds to PIX.

SEQ ID NO:2 is a core sequence within PIX that binds GIT1 and GIT2.

SEQ ID NO:3 is a TAT sequence which confers cell membrane permeability.

SEQ ID NO:4 is the combination of SEQ ID NOs:1 and 3.

SEQ ID NO:5 is a control peptide of SEQ ID NO:4, comprising two amino acid mutations/substitutions.

SEQ ID NO:6 is the combination of SEQ ID NOs:3 and 7, resulting in a PAK/Nck blocking peptide comprising the TAT sequence which confers cell membrane permeability.

SEQ ID NO:7 consists of a sequence from the first proline-rich domain of PAK.

SEQ ID NOs:8-11 are the four sense sequences of the siRNA Smartpool used herein.

In one embodiment, a peptide which is a protein inhibitor comprises the sequence PPPVIAPRPEHTKSVYTR (SEQ ID NO:1) (Manser et al., Mol. Cell. 1998 1:2:183-92), and homologs, modifications, derivatives, analogs and fragments thereof. SEQ ID NO:1 is referred to as the PIX binding sequence.

In another embodiment, the competitive sequence used to inhibit protein complex formation or interaction is AALEEDAQILKVI (SEQ ID NO:2), which is the core sequence within PIX that binds GIT1/2 (corresponding to amino acid residues 685-698 for PIXα and amino acid residues 527-542 for PIXβ; Feng et al., 2002, J. Biol. Chem. 277:5644-5650). In one embodiment, the competitive peptide used comprises one or more of the cores sequences within GIT1 and GIT2 that bind PIX proteins are the Spa2 homology domains (255-375 in GIT1) and the coiled coil regions (428-

485 in GIT1) (Premont et al., 2004, Cell Signal 16: 1001-1011). The region with GIT1 that binds MEK is also within the Spa homology domain and is encompassed within the present invention (amino acid residues 255-375) (Haendeler et al., 2003, J. Biol. Chem. 278:50:49936-44). The TAT sequence, YGRKKRRQRRRG (SEQ ID NO:3) or related polybasic sequences that confer cell membrane permeability to peptides is linked to these sequences (Stockton et al., J. Biol. Chem., 2004, 279:45:46621-46630). Other interaction sites within these proteins that block complex formation or localization to cell-cell junctions and block signaling from PAK to Erk and then to MLCK, are also encompassed within the present invention. In one aspect, more than one peptide, and homologs, modifications, derivatives, analogs and fragments thereof, are used to block complex formation or localization to cell-cell junctions and block signaling from PAK to Erk and then to MLCK. In one aspect of the invention, one or more peptides of the invention is administered with one or more other compounds which regulate vascular permeability.

In one embodiment of the invention, attachment of a polybasic TAT sequence or other permeability sequence to peptides of the invention will allow these constructs to enter cells. In one aspect, the permeabilization sequence is the TAT sequence YGRKKRRQRRRG (SEQ ID NO:3). These conjugated compounds inhibit vascular permeability in injured or inflamed tissues to block edema and tissue injury.

In one embodiment, the invention provides a peptide which is the result of combining SEQ ID NO:3 and SEQ ID NO:1. The combination of SEQ ID NO:3 and SEQ ID NO:1 is SEQ ID NO:4, which is known as the "PIX-binding peptide" herein. The PIX binding peptide is also referred to herein as the "PIX-blocking peptide". SEQ ID NO:4, therefore, has the sequence YGRKKRRQRRRGPPPVIAPRPEHTKSVYTR, which as used herein with the carboxy terminal modification is YGRKKRRQRRRGPPPVIAPRPEHTKSVYTR-K+Biotin.

A control peptide disclosed herein is YGRKKRRQRRRG-PPPVIAPAAEHAKSVVYTR (SEQ ID NO:5), which is also used herein (see FIG. 6) as YGRKKRRQRRRGPPPVIA-PAAEHAKSVVYTR-K+Biotin.

In another embodiment, the competitive sequence used to inhibit protein complex formation or interaction is AALEEDAQILKVI (SEQ ID NO:2), which is the core sequence within PIX that binds GIT1/2 (corresponding to amino acid residues 685-698 for PIXα and amino acid residues 527-542 for PIXβ; Feng et al., 2002, J. Biol. Chem. 277:5644-5650). In one embodiment, the competitive peptide used comprises one or more of the cores sequences within GIT1 and GIT2 that bind PIX proteins, which are the Spa2 homology domains (255-375 in GIT1) and the coiled coil regions (428-485 in GIT1) (Premont et al., 2004, Cell Signal 16:1001-1011). The region with GIT1 that binds MEK is also within the Spa homology domain and is encompassed within the present invention (amino acid residues 255-375) (Haendeler et al., 2003, J. Biol. Chem. 278:50:49936-44). Therefore, the present invention further encompasses peptides comprising the peptides of these domains, and homologs, derivatives, fragments, and modifications thereof. Other interaction sites within these proteins that block complex formation or localization to cell-cell junctions and block signaling from PAK to Erk and then to MLCK, are also encompassed within the present invention. In one aspect, more than one peptide, and homologs, modifications, derivatives, analogs and fragments thereof, are used to block complex formation or localization to cell-cell junctions and block signaling from PAK to Erk and then to MLCK. In one aspect of the invention, one or more peptides of the invention is administered with one or more other compounds which regulate vascular permeability.

In one embodiment of the invention, attachment of a polybasic TAT sequence or other permeability sequence to peptides of the invention will allow these constructs to enter cells. In one aspect, the permeabilization sequence is the TAT sequence YGRKKRRQRRRG (SEQ ID NO:3). These conjugated compounds inhibit vascular permeability in injured or inflamed tissues to block edema and tissue injury.

In one aspect, the TAT-peptide constructs inhibit vascular permeability when contacted with cells. In one aspect, the cells are endothelial cells. In one aspect, the endothelial cells are in culture. In another aspect, the endothelial cells are in vivo.

In one aspect, the present invention provides compositions and methods useful for decreasing vascular permeability or for inhibiting an increase in vascular permeability. In one aspect, the invention provides a composition comprising an inhibitor of protein complex function or activity which may be administered to subjects to treat diseases, disorders, or conditions where vascular leak contributes to, or is caused by, tissue injury, inflammation, edema, swelling, shock, disease, or other conditions or disorders associated with aberrant vascular permeability. Such diseases and injury include, but are not limited to, mechanical or other lung injury, stroke, and myocardial infarction. In one aspect, the invention provides compositions and methods for inhibiting fluid transport in acute lung injury. In another aspect, the present invention provides compositions and methods for decreasing vascular permeability or inhibiting the increase in vascular permeability in a tissue induced by an inflammatory agent in vivo. In one aspect, the tissue is lung tissue. A compound of the invention can also be administered with another drug or medication to a subject in need thereof.

In one embodiment, the invention provides for administration of the peptides of the invention to disrupt the PAK-PIX-GIT-MEK complex and interaction and inhibit vascular permeability due to inflammation and injury in subjects in need thereof. Protein fragments and peptides that compete for the interaction sites to disrupt the PAK-PIX-GIT-MEK complex or displace the complex from cell-cell junctions decrease vascular permeability. These sequences can be fused to the TAT sequence or other sequences that promote transport of proteins into cells. These reagents can be used to inhibit vascular permeability in diseases where vascular leak is a contributing factor. Protein fragments that compete for endogenous interaction sites to block binding of PAK to PIXα or PIXβ, binding of PIX to GIT1 or GIT2, and binding of MEK to GIT1, interrupt the signaling pathway linking PAK to Erk activation and disruption of cell-cell junctions, as well as to MLCK.

In one embodiment, the PAK inhibitor is a short peptide that contains the sequence from PAK that exerts dominant negative activity (Kiosses et al, 2002, Circ. Res. 90:697). This peptide (YGRKKRRQRRRGKPPAPPMRNTSTM; SEQ ID NO:6) consists of the sequence KPPAPPMRNTSTM (SEQ ID NO:7) from the first proline-rich domain of PAK, fused to the polybasic sequence YGRKKRRQRRRG (SEQ ID NO:3) from the HIV TAT protein (Schwarze et al, 1999, Science 285:1569) which promotes entry into cells. The peptide (SEQ ID NO:6) inhibits PAK function similarly to full length dominant negative constructs. The peptide does not block PAK kinase activity per se, but instead displaces PAK from sites of action including cell-cell junctions, which is sufficient to prevent its effects on cellular contractility, migration, and permeability. This peptide is referred to as "PAK-blocking peptide" and "Nck-blocking peptide".

In another embodiment, the PAK inhibitor comprises the autoinhibitory domain of PAK, which blocks PAK kinase activity.

The present disclosure also encompasses other PAK regulators for use in the present invention. Assays useful for identifying additional PAK regulators have been described herein as well as in U.S. Pat. No. 6,248,549 and in U.S. Patent Publication 20040138133, published Jul. 15, 2004, the disclosures of which are incorporated herein in their entirety.

In another embodiment, the regulator of PAK activity or function can block other proteins or molecules from binding with PAK. In one aspect, the regulator binds with the other proteins or molecules and inhibits them from interacting with PAK. In another aspect, the regulator binds to PAK and inhibits other proteins or molecules from binding with PAK.

In one embodiment, the present invention provides methods of inhibiting increased vascular permeability induced by growth factors, cytokines, and bacterial toxins.

One of ordinary skill in the art will appreciate that the inhibitors of the invention can act by competitive inhibition by interacting or binding with a target site of interest, or indirectly by inhibiting the action of a molecule or somehow blocking complex formation or interaction, such as by inducing changes in tertiary structure.

The present invention further provides other types of molecules to disrupt these interactions and signal transduction pathways. In one embodiment, the invention provides isolated nucleic acids comprising nucleic acid sequences encoding peptides of the invention. In another embodiment, the invention provides siRNA directed against proteins of the signal transduction pathways described herein. In one aspect, the siRNA is directed against GIT. In one aspect, the siRNA comprises a sequence selected from the group consisting of SEQ ID NOs:8-11. In another aspect, the inhibitor is an inhibitor of MEK. In one aspect, the inhibitor of MEK is UO126.

In one embodiment, the invention provides a kit for administering at least one peptide of the invention to a subject.

In one embodiment, the invention provides assays and methods for identifying inhibitors of the protein regulatory pathways described herein.

Various aspects and embodiments of the invention are described in further detail below.

A. Mice inhaled aerosolized LPS, with or without prior intraperitoneal injection of 1 mg Nck-blocking peptide (also called PAK blocking peptide; comprising SEQ ID NO:7) or control peptide. At 6 hours, lungs were removed, extracted and analyzed by Western blotting for pSer141 and total PAK2. Two experiments gave similar results.

B. Mice inhaled LPS with control or Nck blocking peptide as in A. At 6 hours, they were injected with Evans blue dye and leakage into the lung assayed at 1 h. Values are means±S.D., n=at least 4. * indicates statistical significance, p<0.01 relative to LPS-treated mice without peptides.

FIG. 2. Erk is downstream of PAK

A. BAECs were pretreated with 20 μg/ml N-terminal PAK peptide that blocks Nck binding, mutated control peptide, or the MEK inhibitor U0126 (25 μM). After 1 hour, 25 ng/ml VEGF was added for 30 minutes. Cells were then fixed and stained for activated Erk.

B. Cells as in A were extracted and analyzed for Erk phosphorylation by Western blotting.

C. BAECs on 3 μm filters were transfected with dominant negative MEK1 (DN MEK), pretreated for 1 hour with 20 μg/ml Pak N-terminal peptide or mutated control peptide, or pretreated with 25 μM U0126. Cells were left untreated or stimulated for 1 h with 25 ng/ml VEGF, 50 ng/ml bFGF, or 10 μM histamine. Leakage of horseradish peroxidase (HRP) across the filter was assayed as described in Methods.

FIG. 3. Erk in vivo.

A. Mice were injected with Nck-blocking peptide (1 mg; comprising SEQ ID NO:7), control peptide (1 mg) or UO126 (0.5 ml of 70 μM), then treated with or without LPS as in FIG. 1. At 6 hours, the lungs were removed, sectioned, and stained for activated Erk using pT202/pY204 antibody. Small arrows indicate unidentified cells in control lungs that stain positively. Large arrows indicate conduit blood vessels.

B. Mice were treated with LPS with or without prior injection of the MEK inhibitor U0126 (0.5 ml of 70 μM). Leakage of Evans blue dye was assayed as in A. * indicates statistical significance, p<0.05 relative to LPS-treated mice without UO126. n=at least 4.

FIG. 4. Requirement for βPIX and GIT1

A. BAECs stimulated with VEGF were fixed and immunostained for GIT1 or βPIX.

B. BAECs were transfected using a nucleoporation protocol that gives 80-90% transfection efficiency with WT GIT1, GIT1 with a SPA2 homology domain (SHD) deletion that does not bind βPIX; WT βPIX; or βPIX with a ΔGBD deletion that does not bind GIT1. Cells were stimulated for 30 minutes with VEGF then fixed and stained for phospho-S141 PAK.

C & D. Cells were transfected as in B and stimulated with VEGF, then detergent extracted and analyzed by Western blotting to detect Erk phosphorylation (C) and myosin light chain (MLC) ser 19 phosphorylation (D).

Figure 5A:
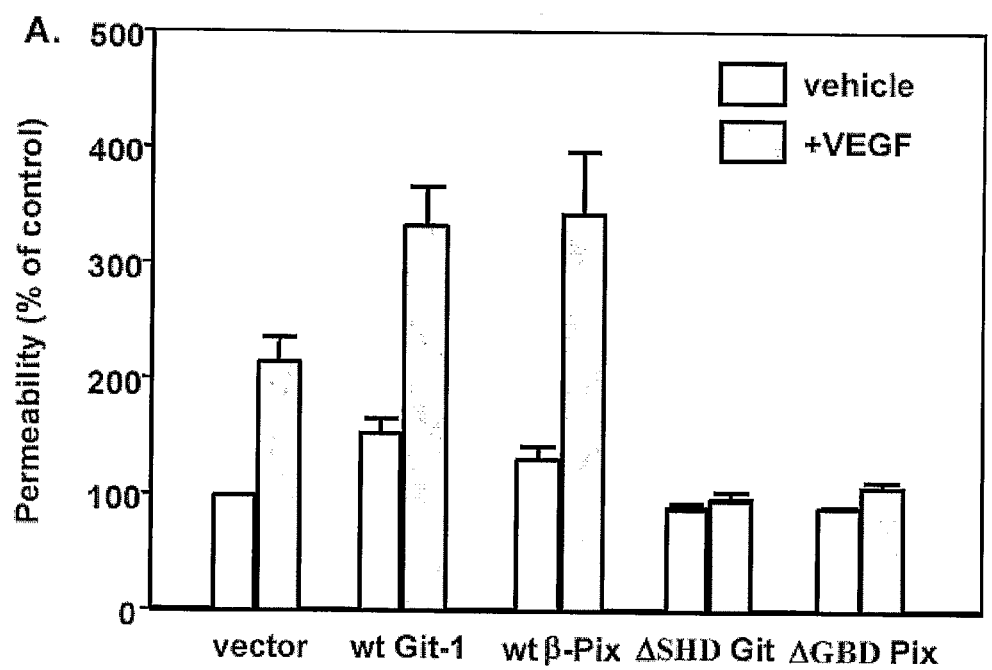

FIG. 5. GIT1 and βPIX control permeability in vitro.

A. Cells transfected as in FIG. 4C were plated on filters with 3.0 μm pores at confluent density. Cultures were stimulated with VEGF and permeability to HRP assayed as described in Methods.

B. HUVECs were transfected with siRNA oligonucleotides specific to GIT1 or with control, scrambled siRNA. Total cell lysates at 72 hours were analyzed for GIT1 expression by Western blotting (top). Cells on filters were analyzed for permeability to HRP after treatment with VEGF (50 ng/ml), histamine (10 μM) or thrombin (0.2 U/ml).

FIG. 6. Blocking the interaction between PAK and PIX.

A. Sequence of the PIX SH3-blocking peptide and the mutated control. The permeabilizing sequence is SEQ ID NO:3, the PIX binding sequence is SEQ ID NO:1, and the combination of the two sequences, the PIX binding peptide, is SEQ ID NO:4. The control peptide for use in conjunction with SEQ ID NO:4 has the sequence SEQ ID NO:5.

B. Cell lysates were incubated with peptides immobilized on streptavidin beads and the whole cell lysates (WCL) or bound proteins analyzed by Western blotting.

C. BAECs were incubated with PIX blocking or control peptide at 20 μg/ml for 1 h, then stimulated with VEGF for 30 min. Cells were rinsed, lysed, and βPIX immunoprecipitated. The IP's were analyzed by Western blotting.

D. BAECs were incubated with peptides and stimulated with VEGF as in C, then lysed and analyzed for Erk activation by Western blotting.

E. Cells incubated with peptides as in C and stimulated with bFGF for 60 min, then stained for F-actin.

Figure 7A:
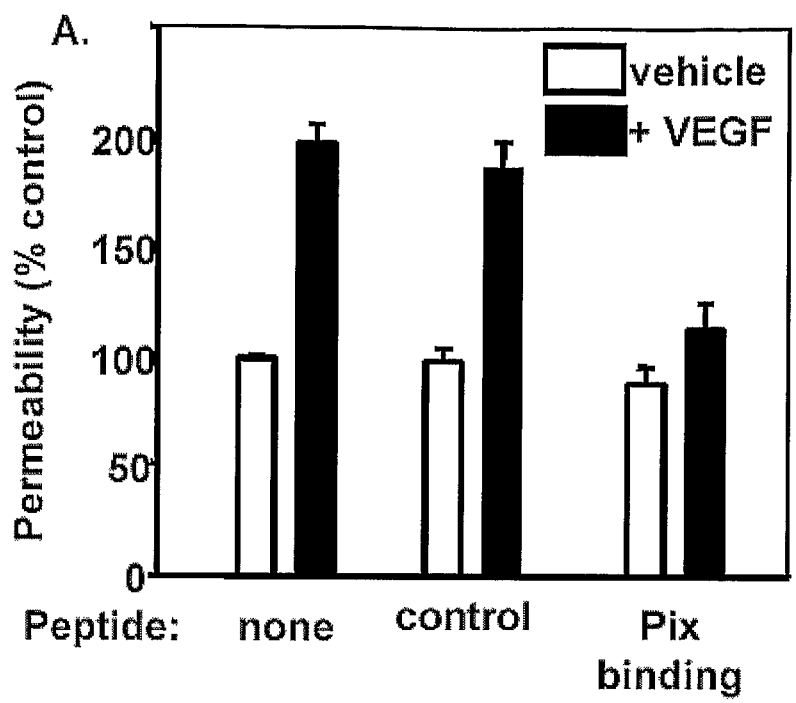

FIG. 7. Peptide blocking of the PIX-PAK interaction.

A. BAECs on filters with 3.0 μm pores were pretreated with 20 μg/ml PIX blocking or control peptides for 1 hour, then stimulated with VEGF for 30 minutes. HRP movement across the monolayer was assayed as described in Methods.

B. Mice received intraperitoneal injections with the indicated amounts of the PIX blocking or control peptides. They were treated with aerosolized LPS for 6 h then leakage of Evans blue dye into the lung assayed as described in Methods. Values are means±S.D., n=4-8. * indicates p<0.02, ** indicates p<0.001, relative to LPS-treated mice without peptides.

C. Lungs from mice pretreated with 1 mg/ml PIX blocking peptide and exposed to LPS as in FIG. 3A were stained for phospho-Erk. See FIG. 3A for comparable untreated and LPS-treated samples. Arrow indicates a conduit vessel.

Figure 8:
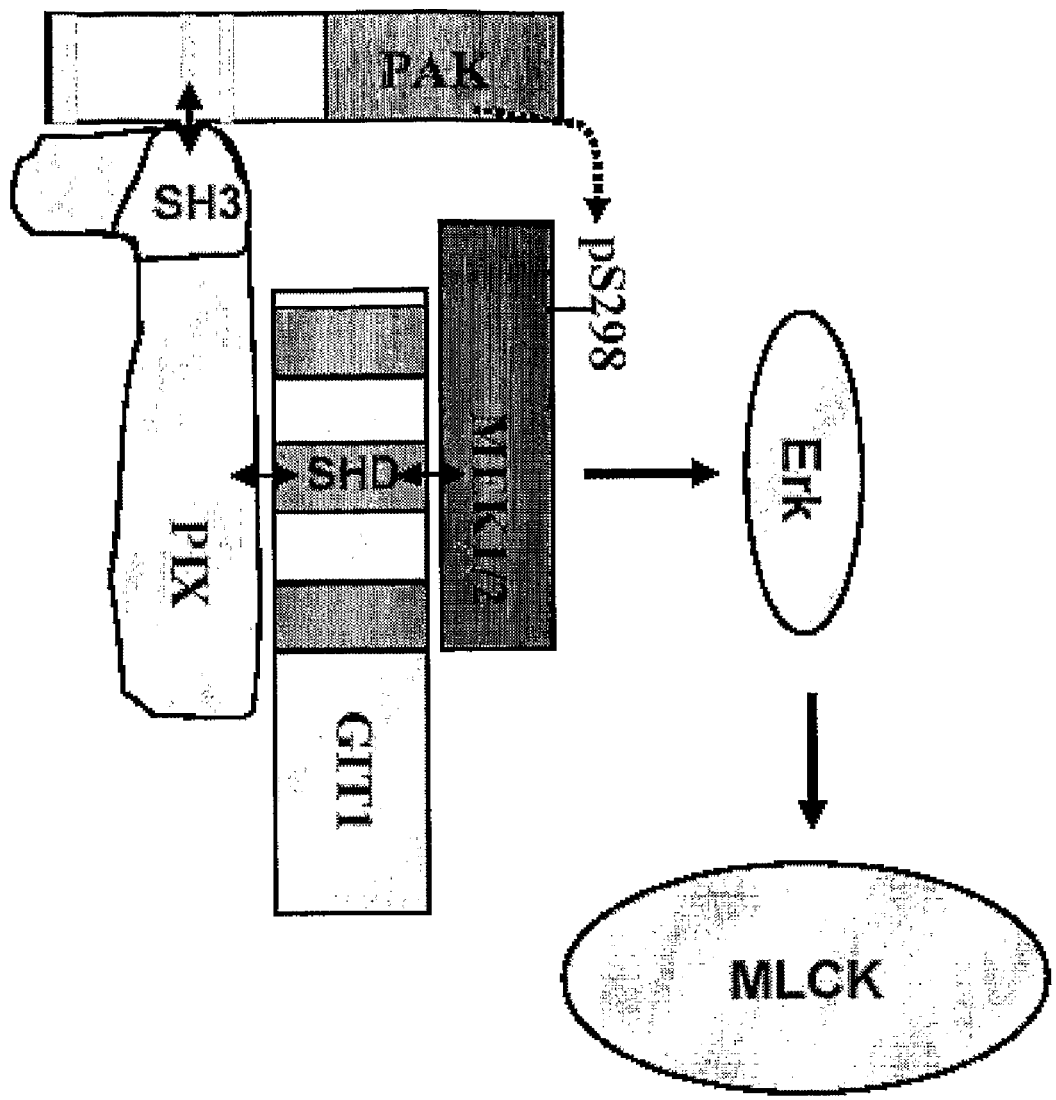

FIG. 8. Model for PAK induction of vascular permeability. PAK is activated in response to inflammatory, thrombotic and angiogenic stimuli. An atypical proline rich sequence in PAK binds to the βPIX SH3 domain. PIX binds to GIT1 through a region in the C-terminus of PIX and the Spa2 homology domain (SHD) of GIT1. The SHD also binds MEK1/2. PAK phosphorylates MEK on ser298, which facilitates activation of MEK by Raf. Subsequent activation of Erk by MEK leads to activation of myosin light chain kinase (MLCK) and contractility, which disrupts intercellular junctions.

DETAILED DESCRIPTION OF THE INVENTION

Abbreviations

AID—autoinhibitory domain
ARF—ADP-ribosylation factor
BAEC—bovine aortic endothelial cells
dn—dominant negative
ECL—enhanced chemiluminescence
ERK—extracellular signal regulated kinase
bFGF—basic fibroblast growth factor
FAK—focal adhesion kinase
FN—fibronectin
GAP—GTPase-activating protein
GIT—GRK-interacting ARF GAP
GRK—G protein-coupled receptor kinase
BRP—horseradish peroxidase
HUVEC—human umbilical vein endothelial cell
ip—intraperitoneal
IP—immunoprecipitation
MEK—MAP/ERK kinases
MLC—myosin light chain
MLCK—myosin light chain kinase
PAK—p21-activated protein kinase
PIX—PAK-interacting exchange factor
PKL—paxillin-kinase linker protein
PBS—phosphate-buffered saline
SHD—Spa2 homology domain
TBS—tris-buffered saline
TNF—tumor necrosis factor
VEGF—vascular endothelial growth factor
WCL—whole cell lysates
wt—wild type

DEFINITIONS

In describing and claiming the invention, the following terminology will be used in accordance with the definitions set forth below.

As used herein, the articles "a" and "an" refer to one or to more than one, i.e., to at least one, of the grammatical object of the article. By way of example, "an element" means one element or more than one element.

The term "adhesion", as used herein, refers broadly to a cell attaching to another cell, molecule, or other substrate.

As used herein, the term "affected cell" refers to a cell of a subject afflicted with a disease, injury, or disorder, which affected cell has an altered phenotype relative to a subject not afflicted with a disease or disorder.

Cells or tissue are "affected" by a disease, injury, or disorder if the cells or tissue have an altered phenotype relative to the same cells or tissue in a subject not afflicted with a disease or disorder.

A disease, condition, or disorder is "alleviated" if the severity of a symptom of the disease or disorder, the frequency with which such a symptom is experienced by a patient, or both, are reduced.

As used herein, "amino acids" are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

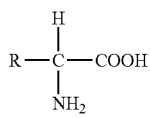

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "antisense oligonucleotide" means a nucleic acid polymer, at least a portion of which is complementary to a nucleic acid which is present in a normal cell or in an affected cell. The antisense oligonucleotides of the invention include, but are not limited to, phosphorothioate oligonucleotides and other modifications of oligonucleotides. Methods for synthesizing oligonucleotides, phosphorothioate oligonucleotides, and otherwise modified oligonucleotides are well known in the art (U.S. Pat. No. 5,034,506; Nielsen et al., 1991, Science 254: 1497). "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, the term "biologically active fragments" or "bioactive fragment" of the polypeptides encompasses natural or synthetic portions of the full-length protein that are capable of specific binding to their natural ligand or of performing the function of the protein.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

The term "competitive sequence" refers to a peptide or a modification, fragment, derivative, or homolog thereof that competes with another peptide for its cognate binding site.

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. As used herein, the terms "complementary" or "complementarity" are used in reference to polynucleotides (i.e., a sequence of nucleotides) related by the base-pairing rules. For example, for the sequence "A-G-T," is complementary to the sequence "T-C-A."

Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "complex", as used herein in reference to proteins, refers to binding or interaction of two or more proteins. Complex formation or interaction can include such things as binding, changes in tertiary structure, and modification of one protein by another, such as phosphorylation.

A "compound," as used herein, refers to any type of substance or agent that is commonly considered a drug, or a candidate for use as a drug, a polypeptide, an isolated nucleic acid, an antibody, or other agent used in the method of the invention, as well as any combination thereof.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "enhancer" is a DNA regulatory element that can increase the efficiency of transcription, regardless of the distance or orientation of the enhancer relative to the start site of transcription.

As used herein, an "essentially pure" preparation of a particular protein or peptide is a preparation wherein at least about 95%, and preferably at least about 99%, by weight, of the protein or peptide in the preparation is the particular protein or peptide.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

The term "inhibit," as used herein, refers to the ability of a compound or any agent to reduce or impede a described function. Preferably, inhibition is by at least 10%, more preferably by at least 25%, even more preferably by at least 50%, and most preferably, the function is inhibited by at least 75%.

The term "inhibit a complex", as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"Operably linked" refers to a juxtaposition wherein the components are configured so as to perform their usual function. Thus, control sequences or promoters operably linked to a coding sequence are capable of effecting the expression of the coding sequence. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "PAK function," as used herein, refers to any activity or function of p21-activated kinase, including, but not limited to, PAK binding with other molecules, kinase activity, autophosphorylation, translocation, activation by other molecules, etc. "PAK function" is used interchangeably with "PAK activity" herein. As used herein, "inhibition of PAK" refers to inhibiting any PAK activity or function, including inhibiting PAK synthesis.

The terms "PAK-blocking peptide", "TAT-PAK-N-terminal peptide" and "Nck-blocking peptide", refer to the peptide of SEQ ID NO:6, and the terms are used interchangeably herein. SEQ ID NO:7, which is a component of SEQ ID NO:

The terms "PIX-blocking peptide", "PIX-binding peptide", and the like as described herein refer to a peptide which blocks the interaction of PAK with PIX, such as the peptide of SEQ ID NO:4, and the terms are used interchangeably herein.

The term "peptide" typically refers to short polypeptides.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

A "recombinant polypeptide" is one which is produced upon expression of a recombinant polynucleotide.

A peptide encompasses a sequence of 2 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH2OC(O)NR—), a phosphonate linkage, a —CH2-sulfonamide (—CH2-S(O)$_2$NR—) linkage, a urea (—NHC(O)NH—) linkage, a —CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O)R2 where R 2 is selected from the group consisting of C1-C4 alkoxy, and —NR3R4 where R3 and R4 are independently selected from the group consisting of hydrogen and C1-C4 alkyl.

The term "permeability," as used herein, refers to transit of fluid, cell, or debris between or through cells and tissues.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., The Peptides, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

The term "regulate" refers to either stimulating or inhibiting a function or activity of interest.

By the term "specifically binds," as used herein, is meant a compound which recognizes and binds a specific protein, but does not substantially recognize or bind other molecules in a sample, or it means binding between two or more proteins as in part of a cellular regulatory process, where said proteins do not substantially recognize or bind other proteins in a sample.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of diagnosis or treatment is a mammal, including a human.

As used herein, the term "treating" includes prophylaxis of the specific disease, disorder, or condition, or alleviation of the symptoms associated with a specific disease, disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The phrase "vascular leak-associated disease or disorder" and the like, as used herein, refers to a disease, disorder, injury, or pathological condition which results in vascular leak or which is associated with vascular leak. Thus, the phrase refers to any condition where vascular-leak occurs. Vascular leak, or changes in vascular permeability, occurs in many diseases, disorders, injuries and pathological conditions. For example, such pathological conditions or stimuli include, but are not limited to, tissue damage, ischemia, inflammation, stroke, wound healing, acute respiratory distress syndrome, hypertension, myocardial infarction, sepsis, hypoxia, infection, allergic reactions, thermal injury, x-irradiation, and ultraviolet irradiation. In addition, vascular leak is associated with local tissue inflammation in many diseases. The term "vascular leak associated disease or disorder" is used interchangeably herein with "vascular permeability associated disease or disorder."

EMBODIMENTS OF THE INVENTION

The present invention is directed to compositions and methods for regulating vascular permeability. The present invention is based, at least in part, on the discovery that blocking PAK function inhibits vascular fluid leak. In one aspect, vascular fluid leak in response to injury is inhibited. The invention further discloses that activity of PAK, such as induction of myosin light chain phosphorylation, is mediated by MEK and Erk. The invention further discloses that Erk is activated via PAK. The invention further discloses that activation of Erk requires the integrity of the complex between PAK, PIX, and GIT1, which in turn acts via MEK. The present invention is therefore directed to means of disrupting the PAK/PIX/GIT1 complex to inhibit stimulation of vascular permeability, as well to as disrupt the complex as it acts via MEK and Erk pathways. The present invention further encompasses inhibiting Erk activation or its pathway as a means to inhibit increased vascular permeability.

In one embodiment, the invention provides a method of inhibiting vascular permeability by blocking the binding of PAK to PIX. In one aspect, the invention provides a peptide that blocks binding of PAK to PIX. In one aspect, the peptide has a sequence comprising a sequence selected from the group consisting of SEQ ID NOs:1 and 4, and homologs, derivatives, and modifications thereof.

In one embodiment, the invention provides a method of inhibiting vascular permeability by inhibiting the interaction of GIT with MEK. The invention provides inhibitors, including, but not limited to, peptides, antibodies, and siRNA.

In one embodiment, the invention provides a method of inhibiting vascular permeability by blocking the binding of PIX to GIT. In one aspect, GIT is GIT1. In another aspect, GIT is GIT2. In one aspect, the invention provides a peptide that blocks binding of PIX to GIT. In one aspect, the peptide comprises the sequence of SEQ ID NO:2. In one aspect, PIX is PIXα. In another aspect, PIX is PIXβ.

The present disclosure also encompasses other PAK regulators for use in the present invention. Assays useful for identifying additional PAK regulators have been described herein as well as in U.S. Pat. No. 6,248,549 and in U.S. Patent Publication 20040138133, the disclosures of which are incorporated herein in their entirety.

In another embodiment, the regulator of PAK activity or function can block other proteins or molecules from binding with PAK. In one aspect, the regulator binds with the other proteins or molecules and inhibits them from interacting with PAK. In another aspect, the regulator binds to PAK and inhibits other proteins or molecules from binding with PAK. In one aspect, an inhibitor of the invention inhibits the interaction of PAK with PIX. In one aspect, the inhibitor is a peptide. In one aspect, the peptide has a sequence comprising SEQ ID NO:4, or a biologically active fragment, homolog, modification, or derivative thereof. In another aspect, the peptide is SEQ ID NO:4, or a biologically active fragment, homolog, modification, or derivative thereof.

In one embodiment the inhibitors of the invention inhibit PIX-GIT complex formation. In another aspect, the function of the PIX-GIT complex is inhibited. In one aspect, an inhibitor of the invention inhibits the PIX-GIT complex from facilitating Erk activation downstream of PAK. In yet another aspect, an inhibitor of the invention inhibits the PIX-GIT complex from facilitating MLCK activation downstream of PAK. In one aspect, the inhibitor is a peptide. In one aspect, the peptide has a sequence comprising SEQ ID NO:4, or a biologically active fragment, homolog, modification, or derivative thereof.

In one embodiment, inhibitors of the invention inhibit formation of the PAK/PIX/GIT complex. In another embodiment, the inhibitors of the invention inhibit the formation or function of the PAK/PIX/GIT/MEK complex.

The present application discloses the use of siRNA for blocking the pathways identified herein. In one aspect, the siRNA is directed against GIT1. In a further aspect, a first siRNA can be used in combination with a second siRNA with a slightly different sequence than the first, or the second siRNA can be directed against a different sequence altogether. In one aspect, the siRNAs directed against GIT1 comprise a sequence selected from the group consisting of SEQ ID NOs:8-11. An siRNA of the invention can be further used with other regulators described herein, or known in the art, such as peptides, antisense oligonucleotides, nucleic acids encoding peptides described herein, aptamers, antibodies, kinase inhibitors, and drugs/agents/compounds.

Many assays and methods are described herein or are known in the art that allow one of ordinary skill in the art to monitor whether a compound regulates the components of the signal transduction and regulatory pathways of PAK, PIX, GIT, MEK, Erk, and MLCK, and these assays and methods are encompassed within the methods of the invention. Such assays are also useful for identifying regulators of the proteins and pathways.

For example, PAK activity and function can be monitored by assaying such things as PAK phosphorylation and translocation to cell-cell junctions. Such assays are described in Schwartz et al. (U.S. Pat. Pub. No. 2005/0233965, Published Oct. 20, 2005; the contents of which are incorporated by reference herein in their entirety). PAK-1, -2, and -3 are held in an inactive conformation via an interaction of the kinase domain with a sequence in the regulatory N terminus named the AID (Bokoch et al., Annu. Rev. Biochem., 2003, 72:743). Binding of activated Rac or Cdc42 to PAK leads to autophosphorylation of several sites that confer sustained increases in PAK kinase activity (Gatti et al., J. Biol. Chem., 1999, 274: 32565; Chong et al., J. Biol. Chem., 2001, 276:17347). One of these sites, $Ser^{141}$ in PAK2 (which corresponds to $Ser^{144}$ in PAK1), is within the AID and its phosphorylation contributes to activation by blocking the interaction of the AID with the kinase domain. To localize activated PAK in endothelial cells, an antibody that specifically recognizes the phosphorylated $Ser^{141}$ site can be used.

To evaluate PAK phosphorylation in endothelial cells in response to a test compound/inhibitor, the compound can be compared to the effects of serum using confluent bovine aortic and human umbilical vein endothelial cells (BAEC and HUVEC, respectively), which can be serum-starved (0.5% serum) for 18 hours and then stimulated with 10% serum. Western blotting with anti-phospho-PAK Ser$^{141}$ antibody can be use to assay changes in PAK phosphorylation. Fluorescence staining of similarly treated cells with anti-phospho-PAK Ser$^{141}$ (pPAK) can be used to indicate changes in PAK phosphorylation in response to serum, no treatment, and the test compound, by assaying whether the activated fraction of the protein localized mainly to cell-cell junctions.

The present invention further encompasses use of the yeast two-hybrid system to identify regulators of the proteins and pathways described herein. Such regulators can be drugs, compounds, peptides, nucleic acids, etc. Such regulators can include endogenous regulators.

Generally, the yeast two-hybrid assay can identify novel protein-protein interactions and compounds that alter those interactions. By using a number of different proteins as potential binding partners, it is possible to detect interactions that were previously uncharacterized. Secondly, the yeast two-hybrid assay can be used to characterize interactions already known to occur. Characterization could include determining which protein domains are responsible for the interaction, by using truncated proteins, or under what conditions interactions take place, by altering the intracellular environment. These assays can also be used to screen modulators of the interactions.

This invention encompasses methods of screening compounds to identify those compounds that act as agonists (stimulate) or antagonists (inhibit) of the protein interactions and pathways described herein. Screening assays for antagonist compound candidates are designed to identify compounds that bind or complex with the peptides described herein, or otherwise interfere with the interaction of the peptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the compound or drug candidate with a peptide identified herein under conditions and for a time sufficient to allow these two components to interact.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with, but does not bind to a particular peptide identified herein, its interaction with that peptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245-246 (1989); Chien et al., Proc. Natl. Acad. Sci. USA, 88:9578-9582 (1991)) as disclosed by Chevray and Nathans, Proc. Natl. Acad. Sci. USA, 89: 5789-5793 (1991). Complete kits for identifying protein-protein interactions between two specific proteins using the two-hybrid technique are available. This system can also be extended to map protein domains involved in specific protein interactions as well as to pinpoint amino acid residues that are crucial for these interactions.

Compounds that interfere with the interaction of a peptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the peptide may be added to a cell along with the compound to be screened for a particular activity and the ability of the compound to inhibit the activity of interest in the presence of the peptide indicates that the compound is an antagonist to the peptide. The peptide can be labeled, such as by radioactivity.

Other assays and libraries are encompassed within the invention, such as the use of Phylomers® and reverse yeast two-hybrid assays (see Watt, 2006, Nature Biotechnology, 24:177; Watt, U.S. Pat. No. 6,994,982; Watt, U.S. Pat. Pub. No. 2005/0287580; Watt, U.S. Pat. No. 6,510,495; Barr et al., 2004, J. Biol. Chem., 279:41:43178-43189; the contents of each of these publications is hereby incorporated by reference herein in their entirety). Phylomers® are derived from sub domains of natural proteins, which makes them potentially more stable than conventional short random peptides. Phylomers® are sourced from biological genomes that are not human in origin. This feature significantly enhances the potency associated with Phylomers® against human protein targets. Phylogica's current Phylomer® library has a complexity of 50 million clones, which is comparable with the numerical complexity of random peptide or antibody Fab fragment libraries. An Interacting Peptide Library, consisting of 63 million peptides fused to the B42 activation domain, can be used to isolate peptides capable of binding to a target protein in a forward yeast two hybrid screen. The second is a Blocking Peptide Library made up of over 2 million peptides that can be used to screen for peptides capable of disrupting a specific protein interaction using the reverse two-hybrid system.

The Phylomer® library consists of protein fragments, which have been sourced from a diverse range of bacterial genomes. The libraries are highly enriched for stable subdomains (15-50 amino acids long). This technology can be integrated with high throughput screening techniques such as phage display and reverse yeast two-hybrid traps.

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals utilizing the technology described in international application no. PCT/US90/02545, which is incorporated by reference herein in its entirety.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (fuse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters. Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), dimethylene-sulfoxide (—CH2-SO—CH2), dimethylene-sulfone (—CH2-SO2-CH2), 2'-O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified.

The term nucleic acid also specifically includes nucleic acids composed of bases other than the five biologically occurring bases (adenine, guanine, thymine, cytosine and uracil).

The present invention is directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring or synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

As used herein, an antagonist or blocking agent may comprise, without limitation, an antibody, an antigen binding portion thereof or a biosynthetic antibody binding site that binds a particular target protein; an antisense molecule that hybridizes in vivo to a nucleic acid encoding a target protein or a regulatory element associated therewith, or a ribozyme, aptamer, or small molecule that binds to and/or inhibits a target protein, or that binds to and/or inhibits, reduces or otherwise modulates expression of nucleic acid encoding a target protein.

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

The present application discloses compositions and methods for inhibiting the proteins described herein, and those not disclosed which are known in the art are encompassed within the invention. For example, various modulators/effectors are known, e.g. antibodies, biologically active nucleic acids, such as antisense molecules, RNAi molecules, or ribozymes, aptamers, peptides or low-molecular weight organic compounds recognizing said polynucleotides or polypeptides.

The present invention is also directed to pharmaceutical compositions comprising the vascular permeability regulatory compounds of the present invention. More particularly, such compounds can be formulated as pharmaceutical compositions using standard pharmaceutically acceptable carriers, fillers, solublizing agents and stabilizers known to those skilled in the art.

The invention is also directed to methods of administering the compounds of the invention to a subject. In one embodiment, the invention provides a method of treating a subject with a vascular-leak or permeability associated disease, disorder, or condition by administering compounds identified using the methods of the invention description. It is preferred that a compound inhibits vascular by at least 10% relative to a control where a compound is not being used to inhibit vascular leak. It is more preferred that a compound of the invention inhibits vascular-leak by at least 25% relative to untreated controls. It is further preferred that a compound of the invention inhibits vascular-leak by at least 50% relative to untreated controls. It is even further preferred that a compound of the invention inhibits vascular-leak by at least 75% relative to untreated controls. It is also preferred that a compound of the invention inhibits vascular-leak by at least 90% relative to untreated controls. In yet another aspect, it is preferred that a compound of the invention inhibits vascular-leak by at least 95% relative to untreated controls. In one aspect of the invention, vascular-leak is inhibited due to inhibition of PAK function or activity. The terms "inhibit" and "block" are used interchangeably herein.

Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a vascular permeability associated disease, disorder, or condition in a subject in need such treatment is provided. The method comprises administering a pharmaceutical composition comprising at least one vascular permeability regulatory compound of the present invention to a patient in need thereof. Compounds identified by the methods of the invention which regulate vascular permeability can be administered with known vascular permeability compounds or other medications as well. Preferably the compounds are administered to a human.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the conditions, disorders, and diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may also be prepared, packaged, or sold in a formulation suitable for rectal administration, vaginal administration, parenteral administration The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parenterally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally, the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1/1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically, dosages of the compound of the invention which may be administered to an animal, preferably a human, range in amount from 1 μg to about 100 g per kilogram of body weight of the subject. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, etc.

The invention also includes a kit comprising a compound of the invention and an instructional material which describes administering the composition to a cell or a tissue of a subject. In another embodiment, this kit comprises a (preferably sterile) solvent suitable for dissolving or suspending the composition of the invention prior to administering the compound to the subject. The invention also provides a kit for identifying a regulator of vascular permeability as described herein, said kit comprising a sample of tissue or cells comprising a p21-activated kinase, a standard regulator of p21-activated kinase, an applicator, and an instructional material for the use thereof.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

The experiments described herein investigated whether Erk might be downstream of PAK in the PAK pathway. A GIT1 construct was used in which the PIX binding region was deleted (GIT1-ΔSHD), and a βPIX construct in which the GIT1 binding region was deleted PIX-ΔGBD in these experiments. Without wishing to be bound by any particular theory, it was hypothesized that the effect of PAK on Erk might require the adapter functions of PIX and GIT. To test this hypothesis, mutants of PIX and GIT were expressed that fail to bind each other, which should remove PAK from the complex by two different means.

Methods

Cell Culture and Transfection

Bovine aortic endothelial cells (BAEC) were grown in low-glucose Dulbecco's Modified Eagles Medium (DMEM) with 10% bovine calf serum (Atlanta Biologicals, Atlanta, Ga.), 100 µg/ml dihydrostreptomycin, and 60 U/ml penicillin (Sigma, St. Louis, Mo.) as described (Stockton 2004). Human umbilical vein endothelial cells (HUVEC) were from Dr. Brett Blackman (University of Virginia) and were grown in EGM-2 medium (Clonetics) supplemented with the manufacturer's "SingleQuot" additions plus 10% fetal bovine serum (Atlanta Biologicals) and were used at passages 3-10.

For some permeabilization assays on filters as indicated in figure legends, confluent BAECs in 0.5% CS-DMEM in 100 mm tissue culture dishes were transfected with 5 µg total of the indicated cDNAs using Effectene, according to the manufacturer's instructions. After incubation overnight, cells were transferred to DMEM with 10% serum and used at 48 h. For some assays, as indicated in legends, cells were transfected by nucleoporation. Cells from two 15 cm plates at 90% confluence were detached and resuspended in 1.5 ml nucleofection buffer (phenol red-free M199 containing 10 mM HEPES). For each transfection, 100 µl cell suspension in 0.2 µl cuvettes received 2.5 µg DNA. Nucleofection was done using the Amaxa Nucleofector II M3 program cycle, after which cells were transferred to 60 mm plates containing 5 ml growth medium and used at 48 h. For immunofluorescence, dishes contained FN-coated glass cover slips. PAK peptides were synthesized by the Biomolecular Research Facility at the University of Virginia or EZ Biolabs Inc. (Westfield Ind.) and were purified by one round of HPLC.

The βPIX and GIT1 constructs were obtained from Dr. A. F. Horwitz. The ΔGBD βPIX (mutated for GIT1 binding) and ΔSHD mutant of GIT1 (mutated for PIX and MEK binding) were as described (Zhang et al., 2003). Dominant negative MEK1 was as described (Renshaw et al., 1997). GIT1 Smartpool siRNA oligos against human sequence were obtained from Dharmacon and the experiments were carried out in HUVECs. The Smartpool mixture contained 4 different siRNA oligos. The four different sense sequences are:

| | |
|---|---|
| 5'GGCCAAAGCUGCUAAGAAGUU3' | (SEQ ID NO: 8) |
| 5'GGACGACGCCAUCUAUUCAUU3' | (SEQ ID NO: 9) |
| 5'GCACACCCAUUGACUAUGCUU3' | (SEQ ID NO: 10) |
| 5'GGACGCCACAUCUCCAUUGUU3'. | (SEQ ID NO: 11) |

LPS-Induced Pulmonary Microvascular Permeability

All animal experiments were approved by the Animal Care and Use Committee of the University of Virginia. Wild type male mice (C57B1/6, 8 to 12 weeks of age, Jackson Labs, Bar Harbor, Me.) were exposed to aerosolized LPS (*Salmonella enteritidis*, Sigma Co., St. Louis, Mo.) for 30 min. This results in a significant increase in microvascular permeability (Reutershan et al., 2005). Control animals inhaled saline. Some mice received intraperitoneal (ip) injection of the PAK inhibitory or control peptides 30 min prior to treatment. To test the role of MEK in vivo, 0.5 ml of 70 µM U0126 was injected ip. Permeability was analyzed at 6 h using the Evans blue dye extravasation technique (Green et al., 1988). Briefly, Evans blue (20 mg/kg; Sigma) was injected intravenously 30 minutes prior to euthanasia. Lungs were perfused through the spontaneously beating right ventricle to remove intravascular dye. Lungs were removed and Evans blue was extracted as described (Peng et al., 2004). The absorption of Evans blue was measured at 620 nm and corrected for the presence of heme pigments: $A_{620}$ (corrected)=$A_{620}$−(1.426×$A_{740}$+0.030) (Wang le et al., 2002). Extravasated Evans blue was calculated against a standard curve (micrograms Evans blue dye per gram lung).

Immunoprecipitation and Western Blotting

Cells were stimulated, washed with cold PBS, extracted with 0.5 ml cold immunoprecipitation (IP) buffer (20 mM Tris pH 7.6, 0.5% NP40, 250 mM NaCl, 5 mM EDTA, 3 mM EGTA; plus Sigma protease and phosphatase inhibitor cocktails) for 10 min. They were passed through an 18 gauge needle 3× and centrifuged for 10 min at 12,000×g in a microfuge. Supernatants were precleared with 25 µl of Protein G-agarose beads and incubated with the indicated primary antibody for 2 hrs at 4°. Anti-phosphoPAk was from Biosource International; anti-total PAK was from Transduction Labs; anti-phospho-Erk and total Erk were from Cell Signaling. Anti-GIT1 and anti-βPIX were from Santa Cruz Biotechnology. 25 µl of protein A- or protein G-agarose beads were added and incubated for another 2 h while rotating at 4° C. Beads were sedimented and washed 3× with 0.5 ml IP buffer and separated by SDS-PAGE. For binding to peptides, 25 µg of biotin-tagged peptides were incubated with 25 µl of streptavidin beads for 30 min, then rinsed and incubated with 0.5 cell lysates for 30 min. Bound proteins were detected by Western blotting with the indicated antibodies. For βPIX, cells were transfected with HA-PIX and blots probed using anti-HA. Proteins were electrophoretically transferred to PVDF membranes, blocked with 5% milk in Tris-buffered saline (TBS) and probed overnight with primary antibodies in the same buffer. Membranes were washed 4×, probed with secondary antibodies for 2 h, and then visualized using chemiluminescence (ECL, Amersham).

In Vitro Permeability

BAECs on FN-coated 3 µm filters at near-confluence were transfected with 0.5 µg cDNA using Effectene as described above. At 48 h, cells were pre-treated for 60 min with PAK peptides as indicated. For some experiments, cells were nucleofected, then plated on filters and grown to confluence for 48 hr. Filters were then placed in outer wells with 500 µl fresh DMEM without phenol red or serum. To each filter well was added 200 µl medium plus 50 µl of 1.5 µg/ml horseradish peroxidase (HRP) with or without cytokines as described. After 30 min, filters were removed and fixed, and the medium in the lower wells assayed for HRP as described (Stockton et al., 2004). Values were normalized to control, untreated wells.

Immunofluorescence

Cells were fixed for 60 minutes in 3.5% formaldehyde, washed, and permeabilized for 10 minutes in 0.2% TX100. Coverslips were blocked with PBS containing 10% goat serum for 60 minutes, then probed 8 hours at 4° C. with 200 µl containing the following antibodies: phospho-ERK at 1:500; phospho-MEK at 1:500; phospho-PAK at 1:500; phospho-MLC at 1:500 (all from BioSource International); βPIX at 1:200 or GIT1 at 1:200 (Santa Cruz Biotechnology). Coverslips were washed and probed overnight at 4° C. with 200 µl anti-mouse IgG-Alexa 568 or anti-rabbit IgG-Alexa 488 (Molecular Probes) at 1:1000. Coverslips were washed and mounted using FluoroMount (Invitrogen).

Immunohistochemistry

Mouse lungs were inflated with an intratracheal instillation of PFA 4% at a constant pressure (20 cm $H_2O$) for 15 minutes. Next, lungs were removed and fixed in PFA 4% for 24 h and embedded in paraffin. Sections (5 µm) were cut for IHC and treated with antigen unmasking solution (Vector Laboratories). Sections were stained with monoclonal rabbit anti p-ERK (1:400 Cell Signaling) overnight and detected with Vectastain Elite Kit (Vector Laboratories). Visualization was done with DAB (Dako Corp) and couterstained with hematoxylin. Images were acquired using 20 or 40× objective on a microscope (model BX51; Olympus) equipped with a digital camera (model DP70 Olympus) using ImagePro software program.

Results

Inhibiting PAK Decreases Fluid Transport in Acute Lung Injury in Mice

Figure 1A:
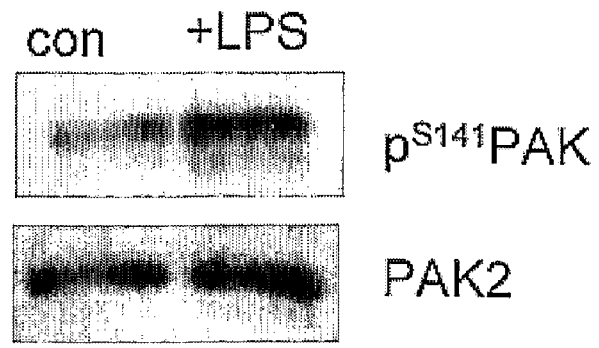
FIG. 1. Vascular permeability in lung inflammation.

Previous work implicated PAK in regulation of endothelial junctional integrity in vitro (Zeng et al., 2000; Stockton et al., 2004) but the relevance to vascular permeability in vivo was not determined. To test whether inhibition of PAK decreases vascular leak in vivo, a mouse model of acute lung injury was employed in which inhalation of aerosolized lipopolysaccharide (LPS) triggers fluid accumulation in the lungs (Reutershan et al., 2005). LPS acts mainly upon resident lung macrophages to trigger release of multiple cytokines. Western blotting using an antibody against a phosphorylation site on PAK that is associated with increased PAK kinase activity showed an increase in phosphorylation in lungs from mice exposed to LPS (FIG. 1A). The normalized increase was 2.1±0.5 fold relative to control, n=2, demonstrating PAK activation in this system.

It was previously found that the inhibitory effect of a full-length dominant negative PAK mapped to the N-terminal proline-rich sequence that binds the SH3 domain of Nck (Kiosses et al., 1999). A peptide in which this sequence was linked to the polybasic sequence from the HIV TAT protein readily enters cells and blocks PAK function similarly to expression of dominant negative PAK (Kiosses et al., 2001). It also inhibited permeability in endothelial cell cultures stimulated with growth factors or inflammatory cytokines (Stockton et al., 2004).

Figure 1B:
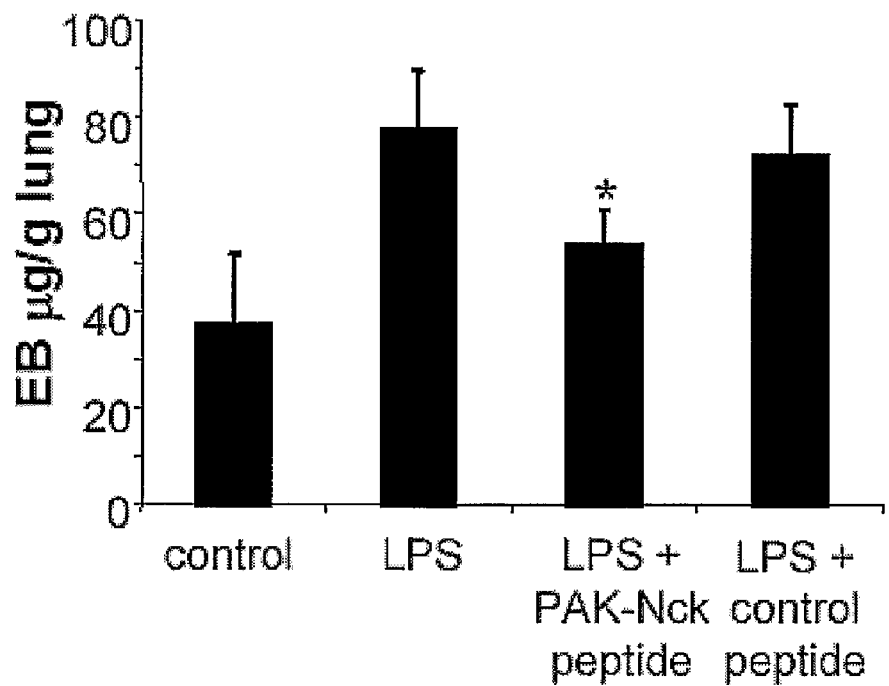

Therefore, mice were injected with the TAT-PAK N-terminal peptide and examined the leakage of Evans blue dye into the lung after inhalation of LPS. The Nck-binding peptide strongly inhibited dye accumulation whereas a control peptide in which two prolines essential for SH3 binding were replaced with alanines had no effect (FIG. 1B). Though it cannot be excluded that this peptide binds other SH3 proteins or affects Nck targets other than PAK, the data suggest a role for PAK in regulating permeability in vivo.

A Role for Erk in Vascular Permeability In Vitro

Figure 2A:
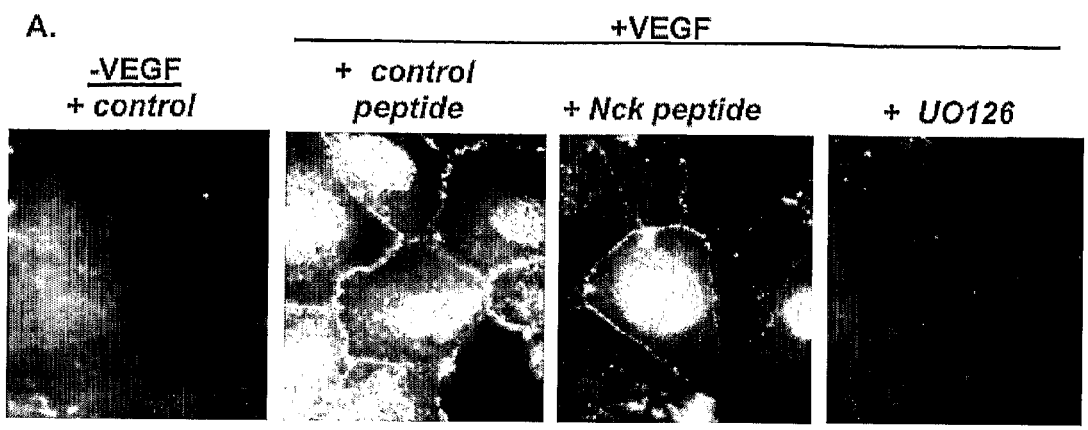
Figure 2B:
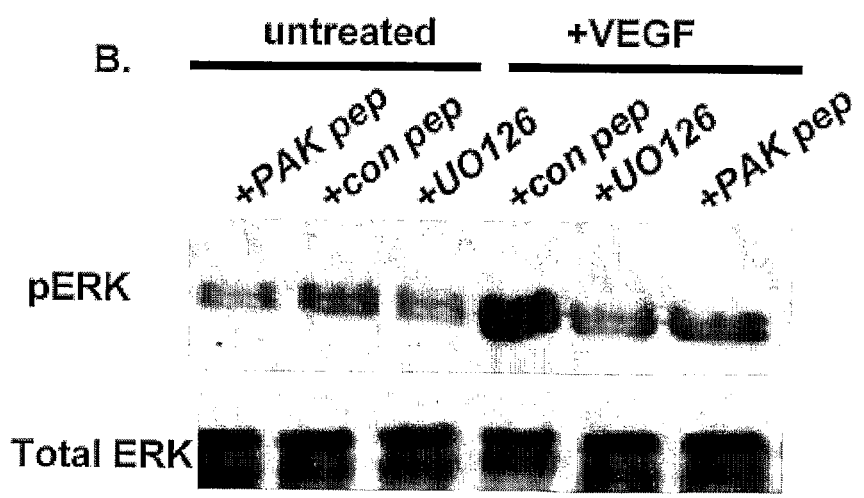

Next, it was considered whether the Erk pathway might be involved. As a first assay, the localization and activation of Erk was determined in confluent bovine aortic endothelial cells in culture. Stimulation with VEGF induced an increase in total staining for activated Erk, with a substantial fraction localized to cell-cell borders (FIG. 2A). This staining was nearly eliminated by pretreatment with the MEK inhibitor UO126, demonstrating that the signal is specific. The PAK inhibitory peptide was then used to test whether Erk was downstream of PAK in this pathway. Western blotting of total cell lysates showed that activation of Erk by VEGF was blocked by the PAK N-terminal peptide nearly as well as by the MEK inhibitor U0126 (FIG. 2B). Immunostaining for activated Erk also showed decreased phosphoErk at cell-cell borders (FIG. 2A). Similar results were obtained with bFGF (not shown).

Figure 2C:
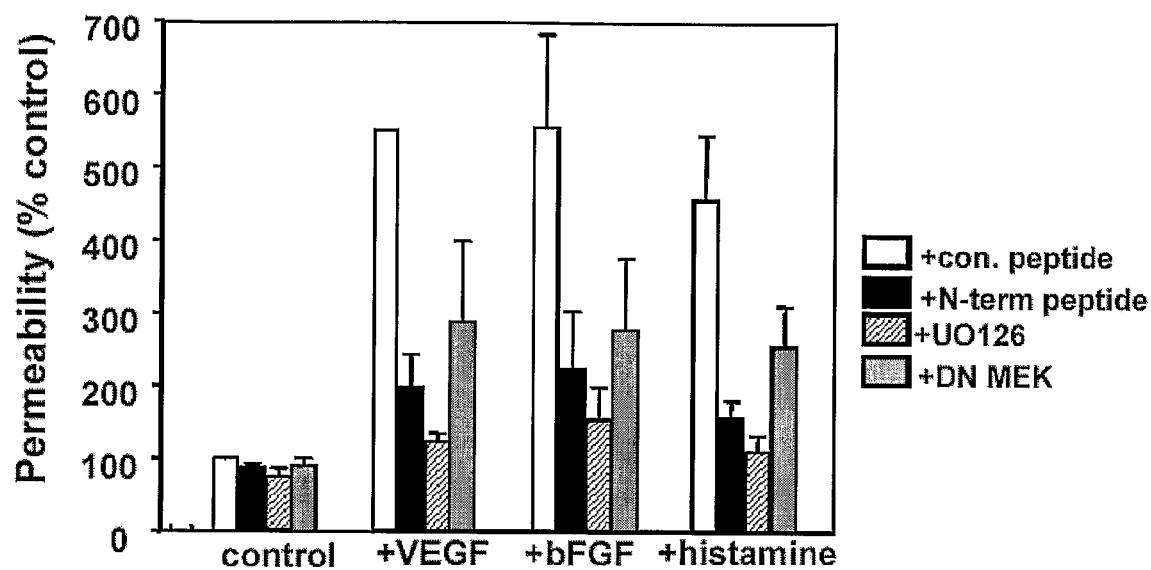

To investigate effects on vascular permeability in vitro, endothelial cells were grown on filters with 3 µm pores and transport of horseradish peroxidase (HRP) across the monolayer was assayed. Permeability induced by VEGF, bFGF or histamine was blocked by UO126 or by transfection with dominant negative MEK, as well as by the PAK N-terminal peptide (FIG. 2C).

Figure 3A:
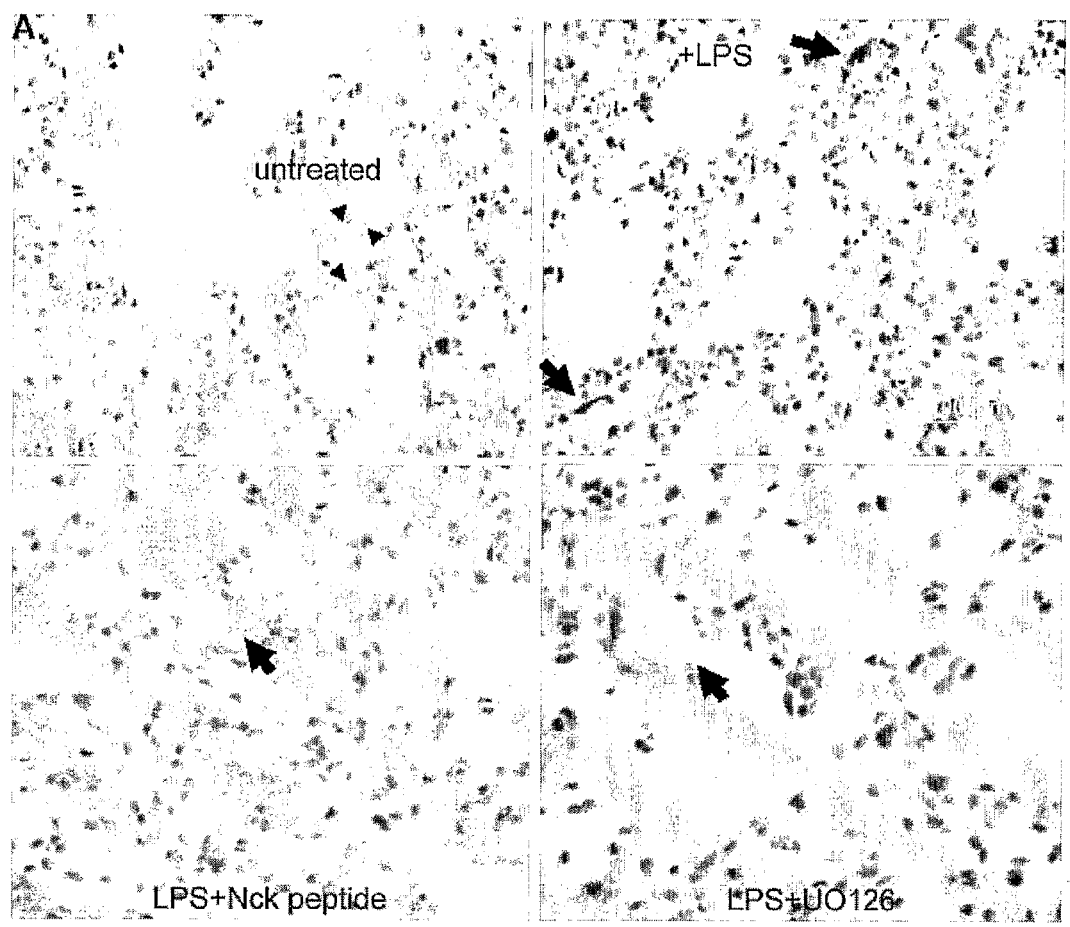
Figure 3B:
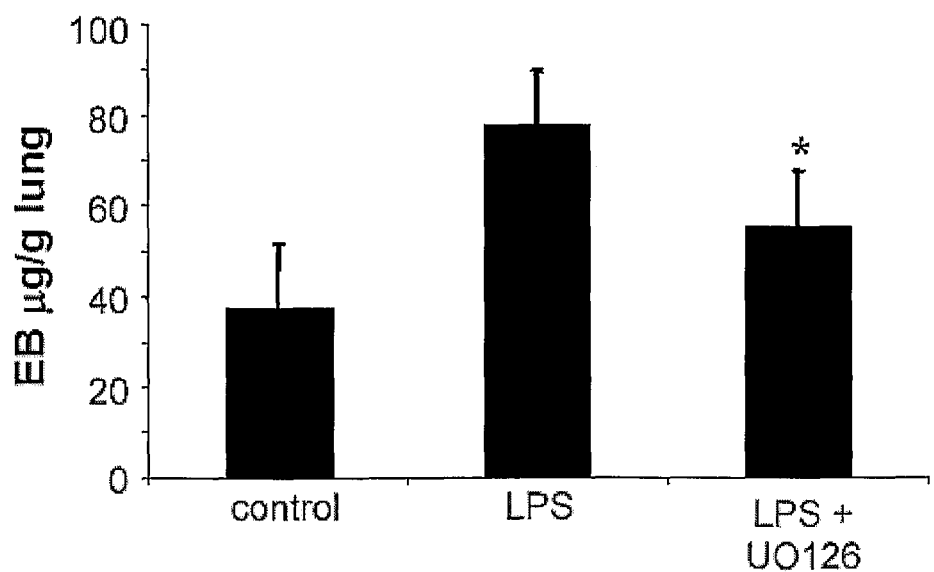

It was then addressed whether these results with cultured endothelial cells were applicable to the vasculature in vivo. First, lung sections were stained with the antibody to phosphoErk. In lungs from untreated mice, most of the lung showed little signal except for sparsely distributed cells in the alveolar wall (small arrows; FIG. 3A). The identity of these cells is unclear, though resident macrophages or dendritic cells seems likely. In LPS-treated mice, there was a marked increase in Erk activation in many cell types, most prominently the vascular endothelium at specific sites along the vessel wall (large arrowheads). Alveolae also stained positively, though less so than blood vessels. This staining may represent alveolar capillaries or epithelium but the specific cell types cannot be resolved by light microscopy. Treatment of mice with the peptide that blocks Nck-PAK interaction largely prevented Erk activation, indicating that Erk is downstream of PAK. As a control, mice were also pretreated with the MEK inhibitor UO126, which also blocked Erk activation throughout the tissue (FIG. 3A). To determine whether Erk is necessary for vascular leak in this system, the effect of UO126 on lung permeability was assayed. The MEK inhibitor significantly blocked the induction of vascular leak by LPS in this model (FIG. 3B). Without wishing to be bound by any particular theory, the data suggest that the MEK-Erk pathway mediates the effect of PAK on vascular permeability.

Involvement of βPIX and GIT1

Next considered was the possibility that specific protein interactions may facilitate the activation of Erk downstream of PAK. PAK is known to associate with PIX proteins through binding of an unconventional proline-rich sequence in PAK to the SH3 domain of PIX (Manser et al., 1998). PIX also contains a central DH/PH module that has nucleotide exchange activity for Rac and Cdc42, and a region near the C-terminus that binds GIT1 (Bagrodia et al., 1999; Zhao et al., 2000). GIT1 contains a Spa2-homology domain (SHD) that binds PIX as well as an ArfGAP domain at its N-terminus (Turner et al., 2001). This SHD region also binds MEK1 and 2 (Premont et al., 2004; Yin et al., 2004). Thus, the PIX-GIT complex has the potential to bring PAK and MEK into proximity, which might facilitate activation of MEK.

Figure 4A:
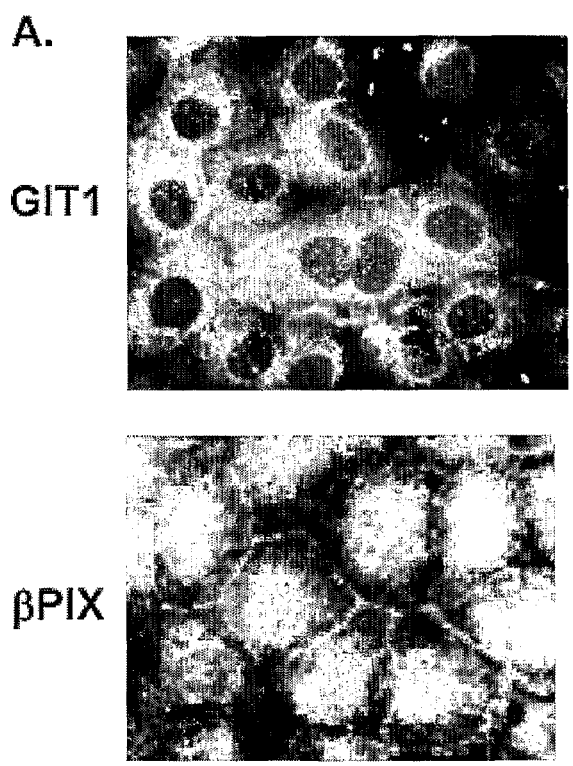
Figure 4B:
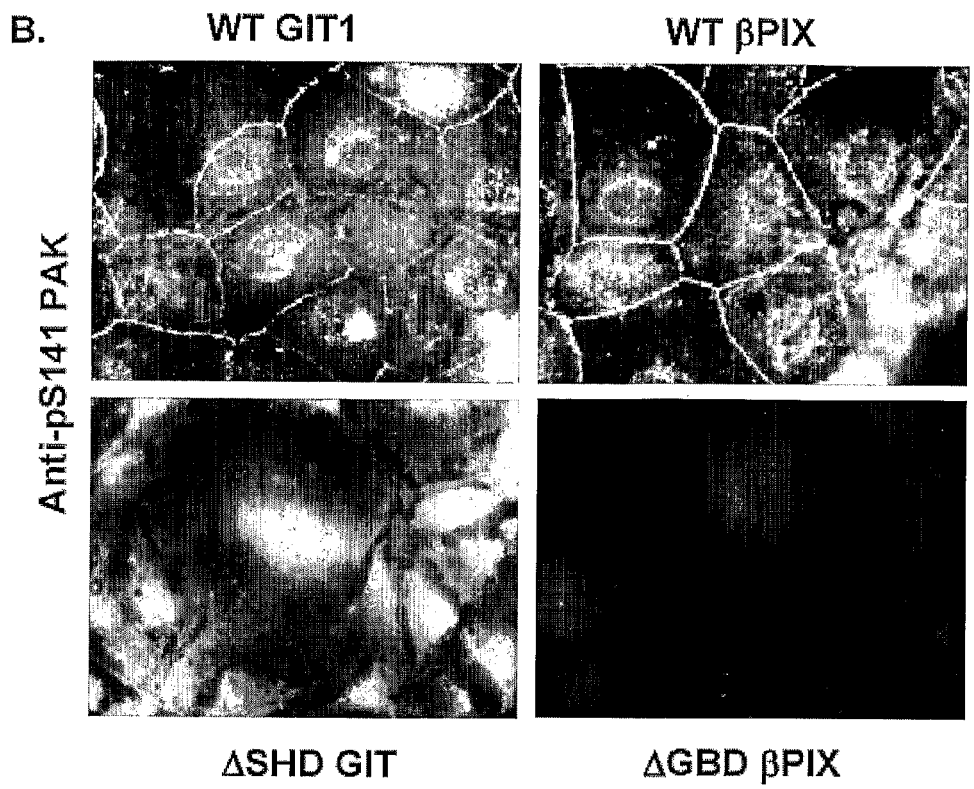
Figure 4C:
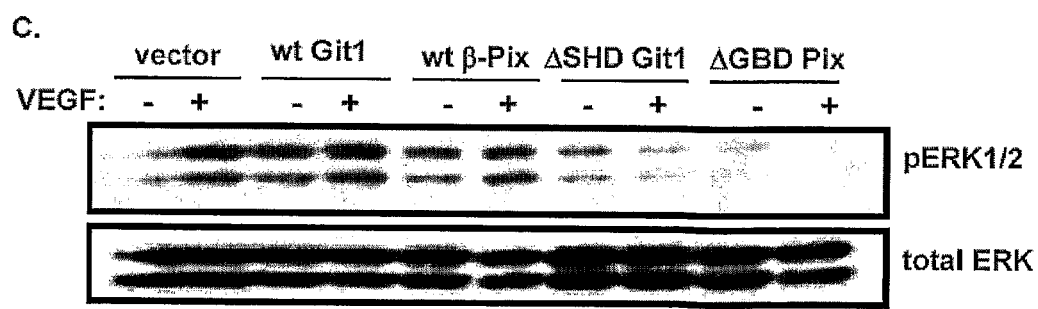
Figure 4D:
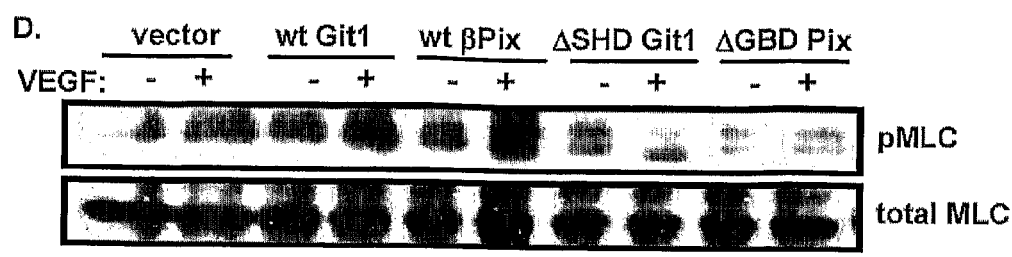

Staining endothelial monolayers with antibodies to βPIX and GIT1 showed that a portion of these proteins were present at cell-cell borders (FIG. 4A). Staining of lung sections also showed expression of both proteins in the endothelium (not shown). To test the functional involvement of these interactions, endothelial cells were transfected with vectors for WT βPIX or a mutant in which the C-terminal GIT-binding region was deleted. Additionally, cells were transfected with WT GIT1 or a mutant in which the SHD that binds PIX and MEK was deleted. Expression of mutant βPIX or GIT1 completely blocked localization of phospho-S141 PAK to cell-cell junctions, whereas the WT constructs had no effect (FIG. 4B). The mutant constructs also blocked activation of Erk and MLC, whereas the WT constructs either increased activation or had no effect (FIGS. 4C and D). Finally, both mutant βPIX and GIT1 efficiently blocked the increase in permeability across an endothelial monolayer in vitro in response to VEGF (FIG. 5A) and bFGF (not shown). By contrast, expression of WT constructs increased permeability. We conclude that the PIX-GIT complex plays a critical role in facilitating Erk and MLC activation downstream of PAK.

Figure 5B:
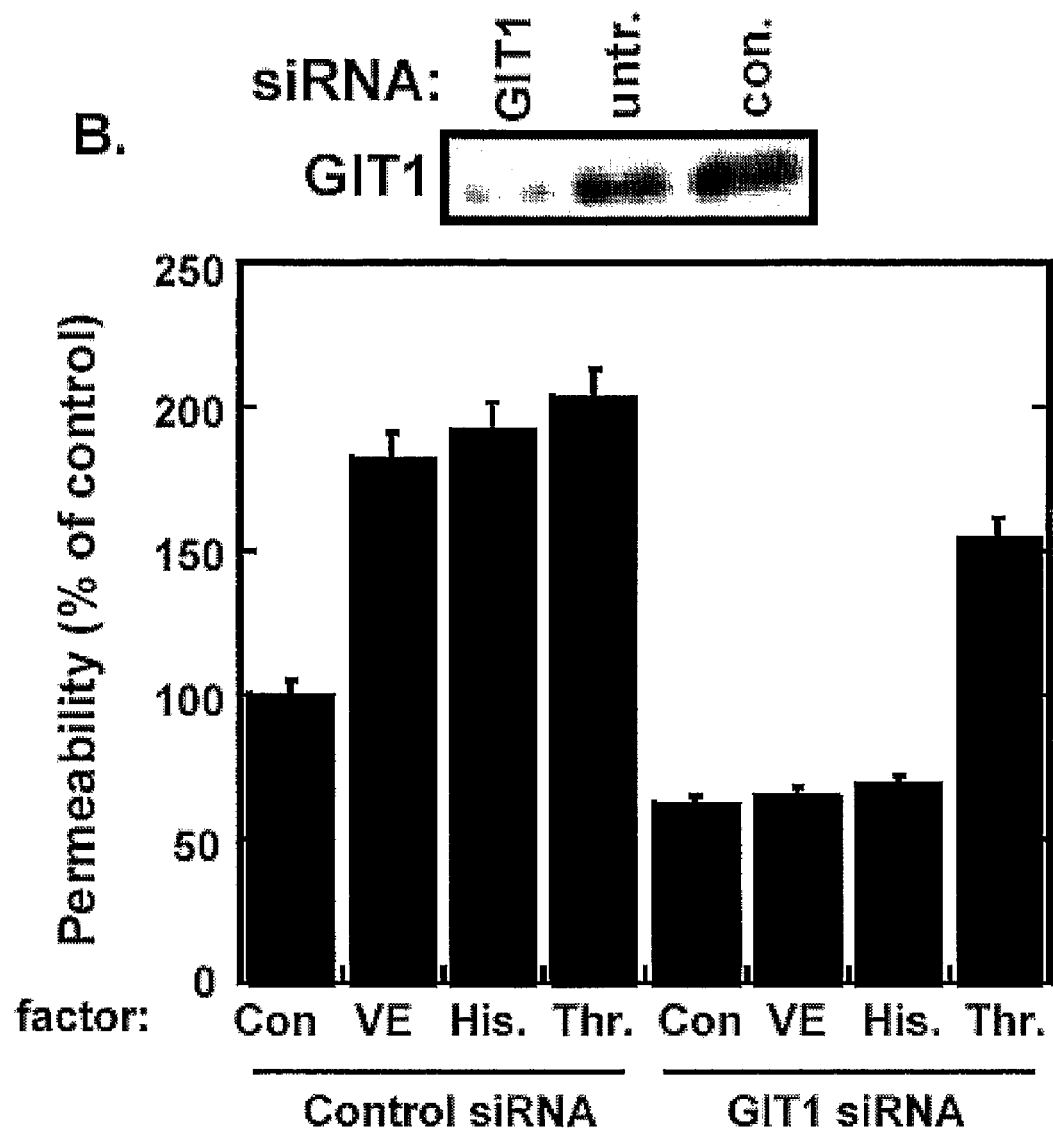

These results may appear to conflict with those from Berk and colleagues who reported that knockdown of GIT1 enhanced vascular permeability in response to thrombin (van Nieuw Amerongen et al., 2004). To address this discrepancy, the effect of GIT1 knockdown on in vitro permeability in response to multiple cytokines was examined herein. In HUVECs, siRNA oligonucleotides targeting GIT1 lowered the baseline and efficiently blocked the increase in permeability induced by bFGF and histamine, but there were no statistically significant effect on thrombin-induced permeability (FIG. 5B). Although the previously observed enhancement of permeability (van Nieuw Amerongen et al., 2004) was not seen in the present studies, it is clear that GIT1 plays a distinct role in the thrombin pathway compared to cytokines. The absence of enhancement may be due to differences in experimental conditions or to different sources of cells.

Peptide Inhibition of the PIX-GIT Complex

Figures 6A, 6B:
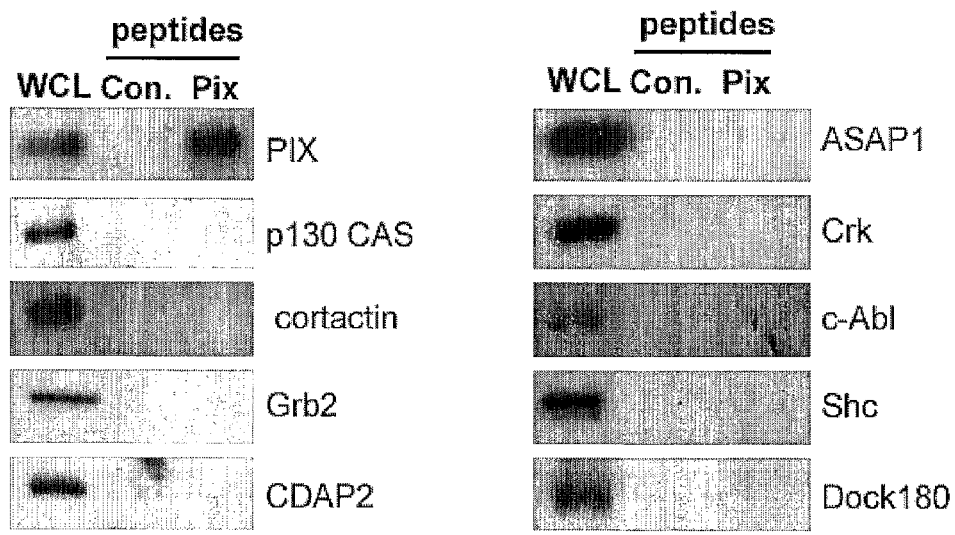

In order to further test the functional relevance of the PAK-PIX-GIT complex, a peptide inhibitor of the PAK-PIX interaction was used (FIG. 6A). PAK binds to the PIX SH3 domain through an atypical proline-rich region that does not fit the consensus sequences for SH3 binding (Manser et al., 1998). To facilitate its entry into cells, a peptide was synthesized in which this sequence was fused to the HIV Tat polybasic region at its N-terminus (Schwarze et al., 1999). We also added a biotin tag to its C-terminus to facilitate detection and immobilization for pull down assays.

When cell lysates were incubated with peptides bound to streptavidin beads, the PIX-binding peptide bound βPIX with high efficiency (FIG. 6B). No binding of βPIX was observed to a control peptide in which two key residues were mutated. A number of other SH3-containing proteins showed no binding, though cortactin showed weak but reproducible binding. When higher amounts of cell lysates were used, weak, specific binding of CD2AP and weak but nonspecific binding of DOCK180 could also be detected (not shown). The peptide therefore appears to be selective for PIX, though does have other, lower affinity interactions.

Figure 6C:
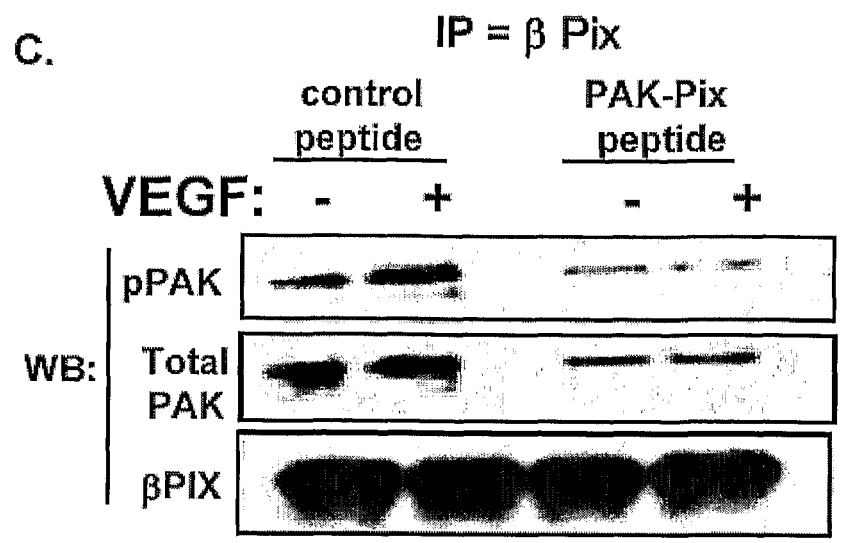
Figure 6D:
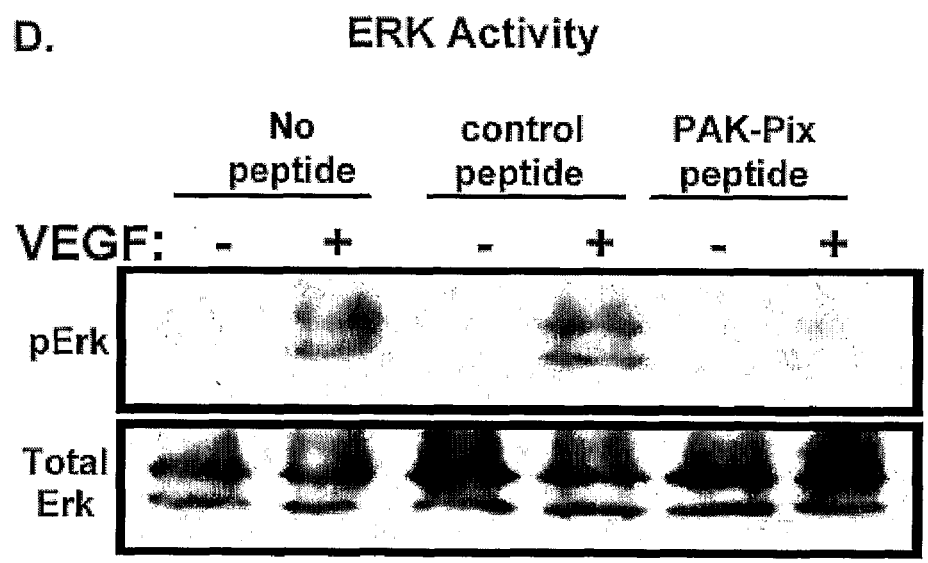
Figure 6E:
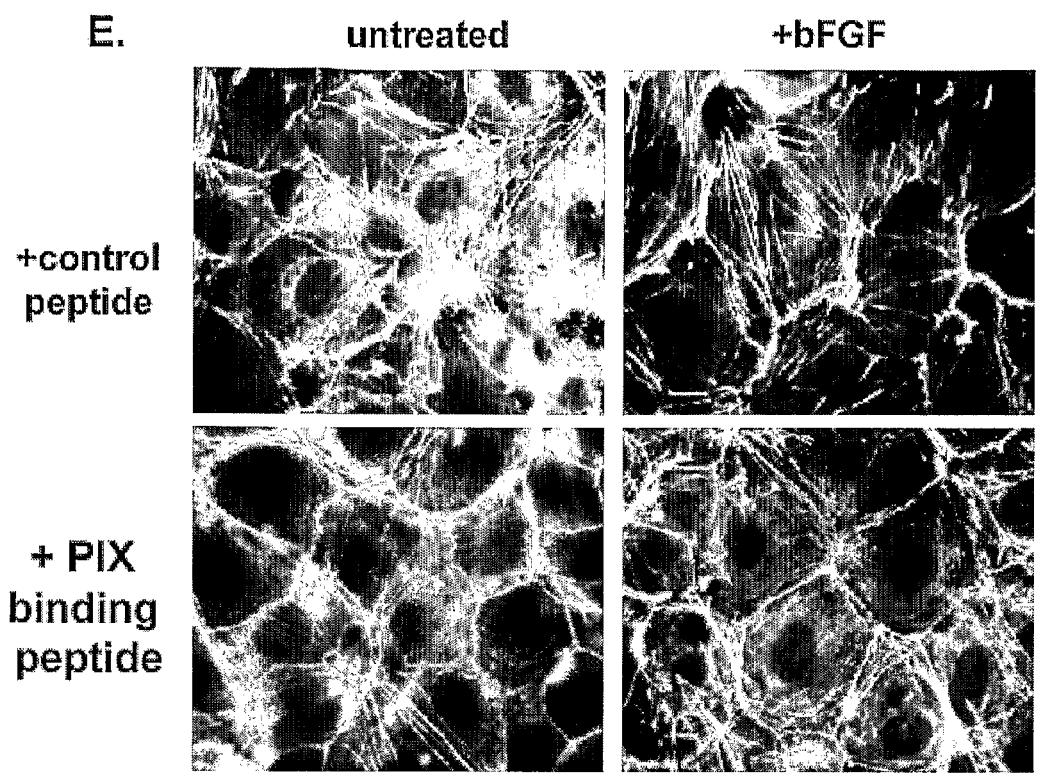

To test its ability to disrupt the interaction between PAK and PIX, endothelial cells were incubated with 20 μg/ml of the PIX binding peptide or the mutated control peptide fused to the TAT sequence to allow entry into cells. The cells were then rinsed, extracted with detergent and βPIX immunoprecipitated. The peptide had no effect on the amount of PIX but reduced the PAK in the precipitates by about 70% (FIG. 6C). This result may underestimate the extent of inhibition since the peptide was washed out before lysis, thus, we cannot exclude that some re-association may have occurred during immune precipitation. When Erk activation was assayed, the PIX blocking peptide efficiently inhibited VEGF-stimulation, whereas the control peptide had no effect (FIG. 6D). Stimulation of Erk by bFGF was also blocked (not shown). Also examined was the reorganization of the actin cytoskeleton in response to bFGF (FIG. 6E) or VEGF (not shown). These growth factors triggered an increase in actin stress fibers in treated cells, which was blocked by the active but not the mutated peptide. The PIX-binding peptide at 20 μg/ml also blocked the increase in permeability in vitro in response to VEGF by approximately 80% in bovine endothelial cells (FIG. 7A) and in HUVECS (not shown). Similar results were obtained for bFGF (not shown).

The PIX Blocking Peptide In Vivo

Figure 7B:
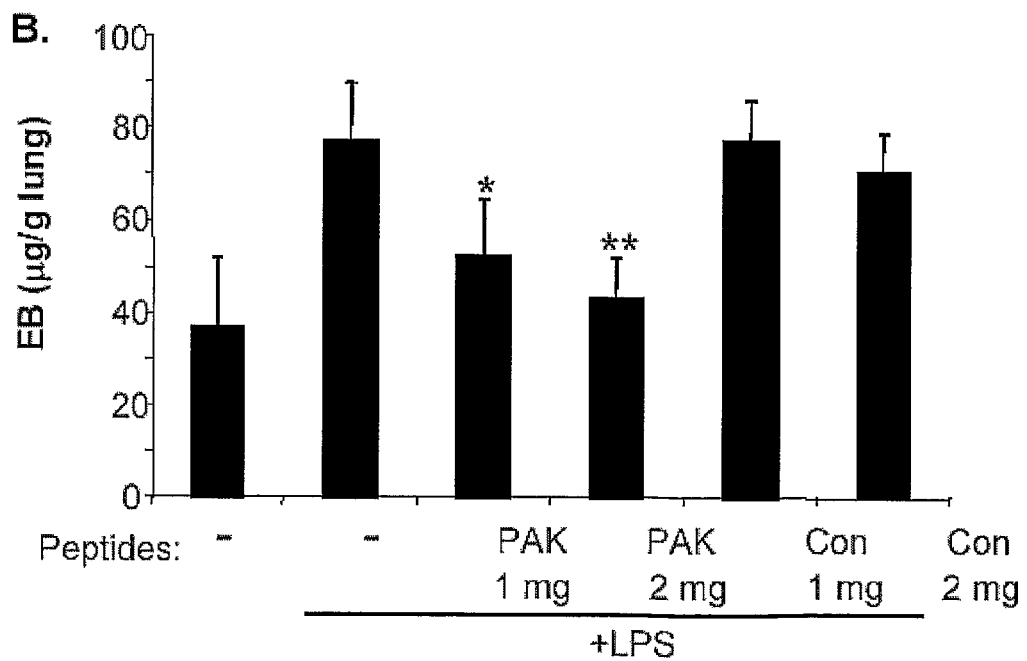
Figure 7C:
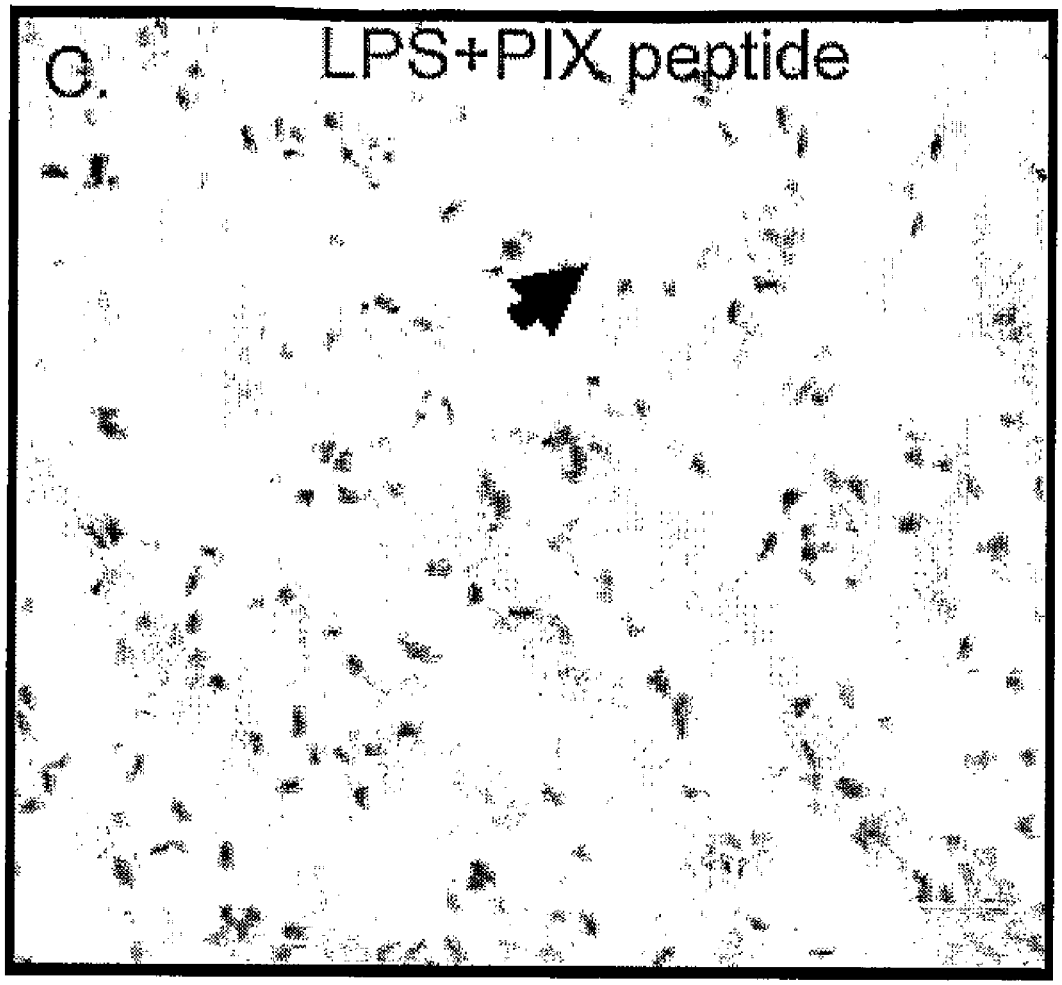

To test whether vascular permeability in vivo requires the interaction between PAK and PIX, mice were examined after inhalation of LPS. For these experiments, TAT-PAK peptides were used that lacked the biotin and the three C-terminal residues, based on an NMR structure showing that these residues did not participate in the interaction with PIX (Mott et al., 2005). Injection of the PIX blocking peptide significantly decreased leakage of Evans blue dye into the lung in a dose-dependent manner (62% inhibition at 1 mg, 85% inhibition at 2 mg), whereas the control peptide had no significant effect (FIG. 7B). Inhibition of phospho-Erk staining was also observed in lung sections (FIG. 7C; compare to FIG. 3A, +LPS sample. Arrowhead indicates a blood vessel). It is concluded herein that the complex between PAK and PIX is required for activation of Erk and induction of vascular leak in an in vivo model of lung inflammation.

CONCLUSIONS

The ability of PAK to activate Erk and induce vascular permeability depends on the integrity of the PAK-PIX-GIT complex. This requirement is relevant to inflammatory, thrombotic and angiogenic mediators. This conclusion is based on co-localization of the relevant components to cell-cell borders and on disruption of the pathway by inhibitory constructs, siRNA-mediated knockdown and cell-permeant peptides. A model, based on current and published data, is shown in FIG. 8. In this model, cytokines trigger activation of PAK (Stockton et al., 2004), which is bound to βPIX. GIT1 binds both PIX and MEK1 or 2 to bring active PAK into proximity with MEK. PAK then phosphorylates MEK on ser298, which enhances MEK binding and activation by Raf (Frost et al., 1997). It is speculated that phosphorylated MEK activates Erk, which activates MLCK to promote myosin-dependent contractility as described previously (Klemke et al., 1997) leading to disruption of cell-cell junctions (Stockton et al., 2004). However, it has also been reported that MEK stimulates vascular permeability independently of Erk (Wu et al., 2005). Without wishing to be bound by any particular theory, it is hypothesized that a specific subfraction of Erk binds to the appropriate scaffolding proteins to mediate these effects. There is precedent for this concept since the small fraction of Erk that localizes to focal adhesions has properties distinct from total active Erk (Hughes et al., 2002).

The activation of PAK in the LPS inhalation model is likely to be due to a cascade involving several cell types that secrete a variety of factors. The focal nature of the Erk activation in the vascular wall suggests that local interactions with leukocytes are likely to be critical. There is evidence that different factors utilize distinct signaling pathways to induce vascular permeability. VEGF, for example, relies on a src-dependant pathway, whereas bFGF does not (Eliceiri et al., 1999). Thrombin effects are mediated mainly by Rho and Rho kinase (Essler et al., 1998; van Nieuw Amerongen et al., 2004). However, PAK and Erk appear to be common signaling intermediates shared by all of these factors. It is interesting that complete knockdown of GIT1 has effects that are distinct from disruption of the PAK-PIX-GIT complex. Although GIT1 knockdown enhances (van Nieuw Amerongen et al., 2004) or has no effect on (present application) thrombin-induced permeability, disruption of the complex clearly blocks. It is likely that other activities of GIT1 are involved in modulating the thrombin response. For example, GIT1 has Arf GAP activity, which can stimulate focal adhesion disassembly (Turner et al., 2001). Consistent with this idea, suppression of GIT1 expression enhanced focal adhesions in thrombin-treated cells (van Nieuw Amerongen et al., 2004). However, specific disruption of PAK-PIX-GIT interactions appears to have distinct effects.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the principles and novel features disclosed herein.

BIBLIOGRAPHY

Bagrodia et al., 1999, J Biol Chem 274, 22393-22400.
Bokoch, G. M., 2003, Annu Rev Biochem 72, 743-781.
Chew et al., 1998, J Muscle Res Cell Motil 19, 839-854.
Eliceiri et al. (1999) Mol. Cell 4, 915-924.
Essler et al., (1998), J. Biol. Chem. 273, 21867-21874.
Foster et al., (2000), J Biol Chem 275, 1959-1965.
Frost et al., (1997), EMBO J. 16, 6426-6438.
Green et al., (1988), J Lab Clin Med 111, 173-183.
Hughes et al., (2002), Mol Biol Cell 13, 2256-2265.
Kimura et al., (2005), Stroke 36, 1259-1263.
King et al., (1998), Nature 396, 180-183.
Kiosses et al., (1999), J. Cell Biol. 147, 831-843.
Kiosses et al., (2001), Circ. Res. 90, 697-702.
Klemke et al., (1997), J. Cell Biol. 137, 481-492.
Lionetti et al., (2005), Curr Opin Crit Care 11, 82-86.
Manser et al., (1998), Mol. Cell. 1, 183-192.
Moff et al., (2005), Biochemistry 44, 10977-10983.
Orfanos et al., (2004), Intensive Care Med 30, 1702-1714.
Paul et al., (2001), Nat. Med. 7, 222-227.
Peng et al., (2004), Am J Respir Crit Care Med 169, 1245-1251.
Premont et al., (2004), Cell Signal 16, 1001-1011.
Renshaw et al., (1997), EMBO J. 16, 5592-5599.
Reutershan et al., (2005), Am J Physiol Lung Cell Mol Physiol 289, L807-815.
Sanders et al., (1999), Science 283, 2083-2085.
Schechtman et al., (2001), Oncogene 20, 6339-6347.
Schwarze et al., (1999), Science 285, 1569-1572.
Scott, (2003, Biochem Soc Trans 31, 87-89.
Stevens et al., (2000), Am J Physiol Lung Cell Mol Physiol 279, L419-422.
Stockton et al., (2004), J Biol Chem 279, 46621-46630.
Turner et al., (2001), Curr Opin Cell Biol 13, 593-599.
van Nieuw Amerongen et al., (2004), Circ Res 94, 1041-1049.
Wang et al., (2002), Am J Respir Crit Care Med 165, 1634-1639.
Wu et al., (2005), J Physiol 563, 95-104.
Yin et al., (2004), Mol. Cell. Biol. 24, 875-885.
Zeng et al., (2000), J Cell Sci 113 (Pt 3), 471-482.
Zhang et al., (2003), J Cell Biol 161, 131-142.
Zhao et al., (2000), Mol. Cell. Biol. 20, 6354-6363.

What is claimed is:

1. A method of inhibiting vascular permeability in a subject having a vascular permeability associated disease or disorder comprising administering to said subject a pharmaceutical composition comprising an effective amount of a peptide selected from the group consisting of SEQ ID NOs: 1, 2 or 4, and a pharmaceutically-acceptable carrier, wherein said peptide inhibits the p21-activated kinase (PAK)-PIX-GIT interaction or complex formation.

2. The method of claim 1, wherein said peptide inhibits an increase in vascular permeability.

3. The method of claim 2, wherein said peptide inhibits a growth factor-stimulated increase in vascular permeability.

4. The method of claim 2, wherein said peptide inhibits a cytokine-stimulated increase in vascular permeability.

5. The method of claim 2, wherein said peptide inhibits a bacterial toxin-stimulated increase in vascular permeability.

6. The method of claim 1, wherein said peptide comprises an amino acid sequence to enhance cell membrane permeability.

7. The method of claim 1, wherein said peptide inhibits the PAK-PIX-GIT interaction or complex formation by inhibiting the interaction or complex formation of PAK-PIX or PIX GIT.

8. The method of claim 7, wherein PIX is PIXα or PIXβ.

9. The method of claim 7, wherein GIT is GIT1 or GIT2.

10. The method of claim 1, wherein said peptide inhibits Erk activation.

11. The method of claim 1, wherein said peptide inhibits MLCK activation.

12. The method of claim 1, wherein said subject has a vascular permeability-associated disease or disorder selected from the group consisting of tissue damage, ischemia, inflammation, stroke, wound healing, acute respiratory distress syndrome, hypertension, myocardial infarction, sepsis, hypoxia, infection, allergic reaction, thermal injury, x-irradiation, and ultraviolet irradiation.

13. The method of claim 1, wherein said vascular permeability-associated disease or disorder is lung inflammation.

* * * * *

SEQUENCE LISTING

<160> NUMBER OF SEQ ID NOS: 11

<210> SEQ ID NO 1
<211> LENGTH: 18
<212> TYPE: PRT
<213> ORGANISM: homo sapiens

<400> SEQUENCE: 1

```
Pro Pro Val Ile Ala Pro Arg Pro Glu His Thr Lys Ser Val Tyr
1               5                   10                  15

Thr Arg

<210> SEQ ID NO 2
<211> LENGTH: 13
<212> TYPE: PRT
<213> ORGANISM: homo sapiens

<400> SEQUENCE: 2

Ala Ala Leu Glu Glu Asp Ala Gln Ile Leu Lys Val Ile
1               5                   10

<210> SEQ ID NO 3
<211> LENGTH: 12
<212> TYPE: PRT
<213> ORGANISM: Human immunodeficiency virus

<400> SEQUENCE: 3

Tyr Gly Arg Lys Lys Arg Arg Gln Arg Arg Arg Gly
1               5                   10

<210> SEQ ID NO 4
<211> LENGTH: 30
<212> TYPE: PRT
<213> ORGANISM: homo sapiens

<400> SEQUENCE: 4

Tyr Gly Arg Lys Lys Arg Arg Gln Arg Arg Gly Pro Pro Val
1               5                   10                  15

Ile Ala Pro Arg Pro Glu His Thr Lys Ser Val Tyr Thr Arg
            20                  25                  30

<210> SEQ ID NO 5
<211> LENGTH: 31
<212> TYPE: PRT
<213> ORGANISM: homo sapiens

<400> SEQUENCE: 5

Tyr Gly Arg Lys Lys Arg Arg Gln Arg Arg Gly Pro Pro Val
1               5                   10                  15

Ile Ala Pro Ala Ala Glu His Ala Lys Ser Val Val Tyr Thr Arg
            20                  25                  30

<210> SEQ ID NO 6
<211> LENGTH: 25
<212> TYPE: PRT
<213> ORGANISM: Homo sapiens

<400> SEQUENCE: 6

Tyr Gly Arg Lys Lys Arg Arg Gln Arg Arg Gly Lys Pro Pro Ala
1               5                   10                  15

Pro Pro Met Arg Asn Thr Ser Thr Met
            20                  25

<210> SEQ ID NO 7
<211> LENGTH: 13
<212> TYPE: PRT
<213> ORGANISM: homo sapiens

<400> SEQUENCE: 7

Lys Pro Pro Ala Pro Pro Met Arg Asn Thr Ser Thr Met
1               5                   10
```

```
<210> SEQ ID NO 8
<211> LENGTH: 21
<212> TYPE: RNA
<213> ORGANISM: homo sapiens

<400> SEQUENCE: 8
ggccaaagcu gcuaagaagu u                                              21

<210> SEQ ID NO 9
<211> LENGTH: 21
<212> TYPE: RNA
<213> ORGANISM: homo sapiens

<400> SEQUENCE: 9
ggacgacgcc aucuauucau u                                              21

<210> SEQ ID NO 10
<211> LENGTH: 21
<212> TYPE: RNA
<213> ORGANISM: homo sapiens

<400> SEQUENCE: 10
gcacacccau ugacuaugcu u                                              21

<210> SEQ ID NO 11
<211> LENGTH: 21
<212> TYPE: RNA
<213> ORGANISM: homo sapiens

<400> SEQUENCE: 11
ggacgccaca ucuccauugu u                                              21
```